(12) United States Patent
Miyake et al.

(10) Patent No.: US 10,280,216 B2
(45) Date of Patent: *May 7, 2019

(54) ANTI-MALIGNANT TUMOR AGENT

(71) Applicant: National University Corporation Okayama University, Okayama (JP)

(72) Inventors: Yasuhiro Miyake, Okayama (JP); Kazuhide Yamamoto, Okayama (JP)

(73) Assignee: National University Corporation Okayama University, Okayama (JP)

( * ) Notice: Subject to any disclaimer, the term of this patent is extended or adjusted under 35 U.S.C. 154(b) by 87 days.

This patent is subject to a terminal disclaimer.

(21) Appl. No.: 15/356,685

(22) Filed: Nov. 21, 2016

(65) Prior Publication Data

US 2017/0073404 A1 Mar. 16, 2017

Related U.S. Application Data

(62) Division of application No. 14/373,038, filed as application No. PCT/JP2013/051275 on Jan. 23, 2013, now Pat. No. 9,567,394.

(30) Foreign Application Priority Data

Jan. 23, 2012 (JP) ................. 2012-010580

(51) Int. Cl.
*C07K 16/18* (2006.01)
*C07K 16/30* (2006.01)
*G01N 33/574* (2006.01)
*A61K 39/00* (2006.01)

(52) U.S. Cl.
CPC .............. *C07K 16/18* (2013.01); *C07K 16/30* (2013.01); *C07K 16/303* (2013.01); *C07K 16/3015* (2013.01); *C07K 16/3023* (2013.01); *C07K 16/3046* (2013.01); *C07K 16/3069* (2013.01); *G01N 33/574* (2013.01); *G01N 33/57484* (2013.01); *A61K 2039/505* (2013.01); *C07K 2317/21* (2013.01); *C07K 2317/73* (2013.01); *G01N 2800/52* (2013.01)

(58) Field of Classification Search
CPC ..................................................... C07K 16/30
USPC ....................................................... 424/184.1
See application file for complete search history.

(56) References Cited

U.S. PATENT DOCUMENTS 9,567,394 B2 * 2/2017 Miyake ............ G01N 33/57484
2015/0004183 A1 1/2015 Miyake et al.

OTHER PUBLICATIONS

International Search Report issued in corresponding International Patent Application No. PCT/JP2013/051275 dated Feb. 26, 2013 (3 pages).

Marzocchella et al., "Spontaneous immunogenicity of ribosomal P0 protein in patients with benign and malignant breast lesions and delay of mammory tumor growth in P0-vaccinated mice," Cancer Science, Mar. 2011, vol. 102, No. 3, pp. 509-515.

Rho et al., "Identification of valid reference genes for gene expression studies of human stomach cancer by reverse transcription-qPCR," BMC Cancer, 2010, vol. 10, p. 240 (13 pages).

Liu et al., "Repression of HIP/RPL29 Expression Induces Differentiation in Colon Cancer Cells," Journal of Cellular Physiology, 2006, vol. 207, pp. 287-292.

Lee et al., "Novel candidate targets of Wnt/beta-catenin signaling in hepatoma cells," Life Sciences, 2007, vol. 80, pp. 690-698.

Garand et al., "An integrative approach to identify YB-1-interacting proteins required for cisplatin resistance in MCF7 and MDA-MB-231 breast cancer cells," Cancer Science, Jul. 2011, vol. 102, No. 7, pp. 1410-1417.

Jung et al., "Clinical Validation of Colorectal Cancer Biomarkers Identified from Bioinformatics Analysis of Public Expression Data," Clinical Cancer Research, Feb. 15, 2011, vol. 17, No. 4, pp. 700-709.

Li et al., "Identification of suitable reference genes for gene expression studies of human serous ovarian cancer by real-time polymerase chain reaction," Analytical Biochemistry, 2009, vol. 394, pp. 110-116.

De Nigris et al., "Overexpression of the HIP Gene Coding for a Heparin/Heparan Sulfate-binding Protein in Human Thyroid Carcinomas," Cancer Research, Oct. 15, 1998, vol. 58, pp. 4745-4751.

Jacobs et al., "Heparin/Heparan, Sulfate Interacting Protein Expression and Functions in Human Breast Cancer Cells and Normal Breast Epithelia," Cancer Research, Nov. 15, 1997, vol. 57, pp. 5148-5154.

Liu et al , "Heparin/heparan sulfate interacting protein plays a role in apoptosis induced by anticancer drugs," Carcinogenesis, 2004, vol. 25, No. 6, pp. 873-879.

(Continued)

*Primary Examiner* — Yan Xiao
(74) *Attorney, Agent, or Firm* — Kilyk & Bowersox, P.L.L.C.

(57) ABSTRACT

The present invention provides an antitumor agent having high safety, which is a molecular target drug against malignant tumors. An anti-malignant tumor agent characterized by containing, as an active ingredient, a substance targeting ribosomal proteins shows increased expression in malignant tumor cells. The substance of the present inventions targeting the ribosomal protein showing increased expression in the malignant tumor cell may be a substance involved in one of biological defense mechanisms which are considered to be intrinsically provided in a living body and prevent onset of disease even if cancer cells develop. Specifically, the ribosomal protein showing increased expression is RPL29 and/or RPS4X. A substance targeting RPL29 and/or RPS4X is an anti-RPL29 antibody and/or anti-RPS4X antibody, a substance capable of activating or enhancing an endogenous anti-RPL29 antibody and/or anti-RPS4X antibody in a living body, a substance capable of inducing production of the anti-RPL29 antibody and/or anti-RPS4X antibody in a living body, or an antagonist of RPL29 and/or RPS4X. Furthermore, the present invention also extends to an examination method of malignant tumors which uses the anti-RPL29 and/or anti-RPS4X antibody titer as an indicator.

11 Claims, 28 Drawing Sheets

(56) References Cited

OTHER PUBLICATIONS

Office Action issued in corresponding Japanese Patent Application No. 2013-555281 dated Oct. 11, 2016 with English translation (8 pages).
International Preliminary Report on Patentability issued in corresponding International Patent Application No. PCT/JP2013/051275 dated May 9, 2014 with English translation (12 pages).
Sawabe et al., "An Inspection Method of p53 Antibody," KENSA to GIJUTSU (Modern Medical Laboratory), 2008, vol. 36, No. 13, pp. 1468-1469 with English translation (9 pages).
Shioda et al., "V. Diagnosis of Hepatocellular Carcinoma, A marker for tumor p53 antibody," Nippon Rinsho—Jpn J. Clin. Med., 2001, vol. 59, Suppl. 6, pp. 356-361 with English translation (12 pages).
Taber's Cyclopedic Medical Dictionary, (1985, F.A. Davis Company, Philadelphia, p. 274) (3 pages).
Buskens et al., "Adenocarcinomas of the Gastro-Esophageal Junction: A Comparative Study of the Gastric Cardia and the Esophagus with Respect to Cyclooxygenase-2 Expression," Digestive Disease Week Abstracts and Itinerary Planner, 2003, Abstract No: 850 (1 page).
Kaiser, "First Pass at Cancer Genome Reveals Complex Landscape," Science, 2006, vol. 313, p. 1370.

\* cited by examiner

Antiproliferative effects of serum IgG on liver cancer cell strain Huh7

**Expressions of RPL29 and RPS4X
in
human liver cancer cell strains**

**Intracellular signal changes
in
liver cancer cell strain Huh7 by a serum IgG**

**Confirmation of expressions of RPL29 and RPS4X
in various human malignant tumor cell strains
(large intestine cancer, small cell lung cancer,
non-small cell lung cancer, breast cancer,
prostate cancer, pancreas cancer)**

Antiproliferative effects of anti-RPL29 antibody on liver cancer cell strain Huh7

Serum anti-RPL29 antibodies in patients
with unresectable pancreas cancer

Serum anti-RPL29 antibody titers
and survival durations
in patients with unresectable pancreas cancer

Antiproliferative effects of anti-RPL29 antibody on liver cancer cell strain PLC/PRF/5

**Serum anti-RPL29 antibody titer
and antiproliferative effects of serum IgG
on liver cancer cell strain Huh7**

**Serum anti-RPL29 antibody titer
and antiproliferative effects of serum IgG
on liver cancer cell strain PLC/PRF/5**

**Serum anti-RPL29 antibody titer
and antiproliferative effects of serum IgG
on cultured liver cancer cell Huh7**

**Serum anti-RPL29 antibody titer
and antiproliferative effects of serum IgG
on cultured liver cancer cell PLC/PRF/5**

Antiproliferative effects of anti-RPL29 antibody on pancreas cancer cell strain Panc-1

Antiproliferative effects of anti-RPL29 antibody on pancreas cancer cell strain AsPC-1

**Intracellular signal changes
in pancreas cancer cell strain AsPC-1
by anti-RPL29 antibody**

Serum anti-RPL29 antibodies
in postoperative patients with pancreas cancer

Serum anti-RPL29 antibody titers
and postoperative recurrences
in patients with pancreas cancer

Antiproliferative effects of serum IgG of AIH-31 (serum anti-RPL29 antibody titer: 1.847 OD405 nm) on pancreas cancer and large intestine cancer

Antiproliferative effects of serum IgG of AIH-45 (serum anti-RPL29 antibody titer: 1.716 OD405 nm) on pancreas cancer and large intestine cancer

**Antitumor effects of serum IgG of AIH-31
(serum anti-RPL29 antibody titer: 1.847 OD405 nm)**

**Antitumor effects of serum IgG of AIH-45
(serum anti-RPL29 antibody titer: 1.716 OD405 nm)**

Antiproliferative effects of anti-RPL29 antibody on malignant tumor cells

Antiproliferative effects of anti-RPS4X antibody on liver cancer cell strain Huh7

Antiproliferative effects of anti-RPS4X antibody on malignant tumor cells

Antiproliferative effects of anti-RPS4X antibody on malignant tumor cells

ANTI-MALIGNANT TUMOR AGENT

The present application is a divisional application of U.S. patent application Ser. No. 14/373,038, filed Jul. 18, 2014, which is a National Stage Application of PCT/JP2013/051275, filed Jan. 23, 2013, which claims priority from Japanese Patent Application No. 2012-010580, filed Jan. 23, 2012.

TECHNICAL FIELD

The present invention relates to a novel antitumor agent which contains, as an active ingredient, a substance targeting ribosomal proteins showing increased expression in malignant tumor cells. Furthermore, the present invention relates to a production method of the substance targeting ribosomal proteins contained, as an active ingredient, in the novel antitumor agent.

The present application claims priority of Japanese Patent Application No. 2012-010580, which is incorporated herein by reference.

BACKGROUND ART

As current molecular target drugs against malignant tumors, there have been developed and used, in practical clinic, many agents such as sorafenib used for liver cancer and renal cancer, cetuximab and bevacizumab used for large intestine cancer, erlotinib and gefitinib used for lung cancer, and trastuzumab used for breast cancer. As target substances of each agent, there can be exemplified cancer kinase, vascular endothelial growth factor (VEGF), epidermal growth factor receptor (EGFR), HER2 protein, and the like. However, in relation to molecular target drugs against malignant tumors, there have also been reported skin disorder, gastrointestinal perforation, interstitial pneumonia, and deaths due to severe side effects such as liver failure. Therefore, appearance of a safer molecular target drug is desired. Meanwhile, although it is said that even healthy persons have thousands of malignant tumor (cancer) cells every day, everyone does not necessarily develop disease. It has been reported that incidence of liver cancer in autoimmune hepatitis (AIH) is about 0.7%/year (Aliment Pharmacol Ther 2006; 24:1197) and is obviously lower than 3%/year in chronic hepatitis C (Ann Intern Med 1999; 131:174).

It has been reported that a ribosomal protein RPL29 (Ribosomal protein L29) shows increased expression in cells of various malignant tumors such as large intestine cancer (Non Patent Literature 1), liver cancer (Non Patent Literature 2), gastric cancer (Non Patent Literature 3), thyroid cancer (Non Patent Literature 4) and breast cancer (Non Patent Literature 5). The RPL29 is a membrane protein expressed on a cell surface, and it has been reported that when the expression of the RPL29 is lowered, cells causing apoptosis are increased (Non Patent Literature 6), and cellular differentiation is induced (Non Patent Literature 1). In addition, it has been reported that a ribosomal protein RPS4X (Ribosomal protein S4, X-linked) shows increased expression in cells of various malignant tumors such as large intestine cancer (Non Patent Literature 7) and breast cancer (Non Patent Literature 8). However, it has not been reported that a substance targeting the ribosomal proteins RPL29 and RPS4X improved tumors.

CITATION LIST

Non Patent Literature

[NPL 1] J Cell physiol., 2006; 207 (2): 287-92
[NPL 2] Life Sci. 2007 Jan. 23; 80 (7): 690-8. Epub 2006 Dec. 6
[NPL 3] BMC Cancer, 2010; 10: 240
[NPL 4] Cancer Res., 1998; 58: 4745
[NPL 5] Cancer Res., 1997; 57: 5148
[NPL 6] Carcinogenesis, 2004; 25 (6): 873-879
[NPL 7] Clin Cancer Res., 2011; 17 (4): 700-9. Epub 2011 Feb. 8.
[NPL 8] Cancer Sci., 2011; 102 (7): 1410-7

SUMMARY OF INVENTION

Technical Problem

An object of the present invention is to provide an antitumor agent having high safety, which is a molecular target drug against malignant tumors.

Solution to Problem

As results of the multiple earnest researches for solving the problem, the present inventors have focused on the fact that although even healthy persons are said to have thousands of malignant tumor (cancer) cells everyday, everyone does not necessarily develop cancer, and that there has been a report of the incidence of liver cancer in autoimmune hepatitis (AIH) being about 0.7%/year and the incidence is obviously lower than 3%/year in chronic hepatitis C. In addition, the present inventors have found that an immunoglobulin (IgG) capable of suppressing growth of malignant tumor cells is present in serum of patients with autoimmune hepatitis, and have completed the present invention.

That is, the present invention includes the following matters.

1. An anti-malignant tumor agent containing, as an active ingredient, a substance targeting a ribosomal protein showing increased expression in a malignant tumor cell.
2. The anti-malignant tumor agent according to the preceding item 1, wherein the ribosomal protein showing increased expression in the malignant tumor cell is an RPL29 and/or RPS4X.
3. The anti-malignant tumor agent according to the preceding item 2, wherein a substance targeting the RPL29 is an anti-RPL29 antibody, a substance capable of activating or enhancing an endogenous anti-RPL29 antibody existing in a living body, a substance capable of inducing production of the anti-RPL29 antibody in the living body, or an RPL29 antagonist.
4. The anti-malignant tumor agent according to the preceding item 2, wherein a substance targeting RPS4X is an anti-RPS4X antibody, a substance capable of activating or enhancing an anti-RPS4X antibody existing in a living body, a substance capable of inducing production of the anti-RPS4X antibody in the living body, or an RPS4X antagonist.
5. The anti-malignant tumor agent according to the preceding item 3 or 4, wherein the substance capable of activating or enhancing the endogenous anti-RPL29 antibody and/or anti-RPS4X antibody existing in the living body is an immunostimulator, and the substance capable of inducing production of the anti-RPL29 antibody and/or anti-RPS4X antibody in the living body is a vaccine.

6. The anti-malignant tumor agent according to any one of the preceding items 1 to 5, wherein the malignant tumor is one or a plurality of cancers selected from liver cancer, pancreas cancer, breast cancer, large intestine cancer, non-small cell lung cancer, small cell lung cancer, prostate cancer, gastric cancer, thyroid cancer, ovarian cancer, salivary gland adenoid cystic carcinoma, acute myeloid leukemia, acute lymphocytic leukemia, chronic lymphocytic leukemia, chronic myeloid leukemia, malignant lymphoma, myxoidliposarcoma, glioblastoma, alveolar rhabdomyosarcoma, Wilms tumor, oligodendroglioma, adrenocortical carcinoma, multiple myeloma, medulloblastoma, endometrial cancer, esophageal cancer and Ewing's sarcoma.

7. An examination method of malignant tumors, wherein an anti-RPL29 antibody titer and/or an anti-RPS4X antibody titer in a biospecimen is measured.

8. The examination method according to the preceding item 7, wherein the examination of malignant tumors is a prediction of prognosis of the malignant tumors.

9. The examination method according to the preceding item 7 or 8, wherein the malignant tumor is one or a plurality of cancers selected from liver cancer, pancreas cancer, breast cancer, large intestine cancer, non-small cell lung cancer, small cell lung cancer, prostate cancer, gastric cancer, thyroid cancer, ovarian cancer, salivary gland adenoid cystic carcinoma, acute myeloid leukemia, acute lymphocytic leukemia, chronic lymphocytic leukemia, chronic myeloid leukemia, malignant lymphoma, myxoid liposarcoma, glioblastoma, alveolar rhabdomyosarcoma, Wilms tumor, oligodendroglioma, adrenocortical carcinoma, multiple myeloma, medulloblastoma, endometrial cancer, esophageal cancer and Ewing's sarcoma.

Advantageous Effects of the Invention

The anti-malignant tumor agent of the present invention which contains, as an active ingredient, a substance targeting ribosomal proteins showing increased expression in a malignant tumor cell can suppress growth of the malignant tumor cells. The substance of the present inventions targeting to the ribosomal protein showing increased expression in the malignant tumor cell may be a substance involved in one of biological defense mechanisms which are considered to be intrinsically provided in a living body and which prevents onset of disease even if malignant tumor cells develop. An anti-malignant tumor agent which contains such a substance as an active ingredient is a drug having high safety and is useful.

Additionally, in the examination method of the present invention, a prognosis of a cancer patient can also be predicted by measuring an amount of the substance targeting ribosomal proteins showing increased expression in a malignant tumor cell, for example, by measuring an antibody titer in a case of an antibody, and the anti-malignant tumor agent is very useful in being able to provide the cancer patient with an optimal therapy in accordance with the results.

DESCRIPTION OF EMBODIMENTS

Figure 1:
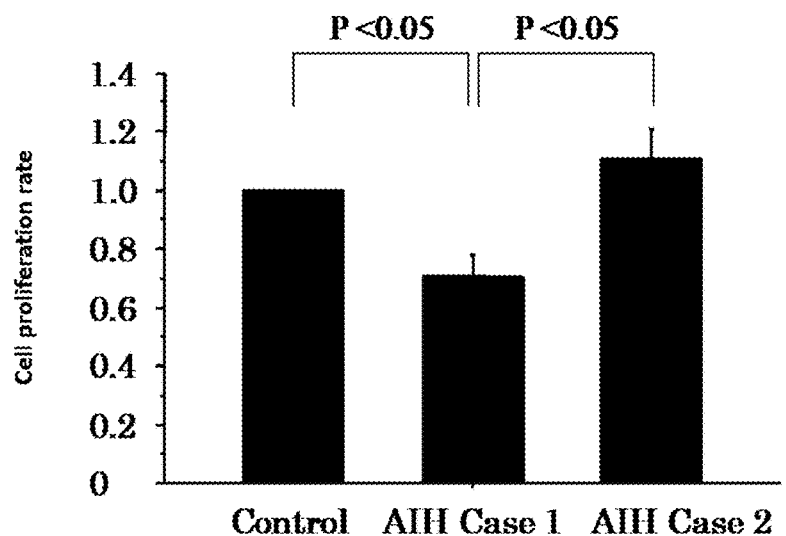
FIG. 1 A diagram showing antiproliferative effects of a serum IgG on liver cancer cell strain Huh7 (Reference Example 1).

The present invention relates to an anti-malignant tumor agent having high safety, which is a molecular target drug against malignant tumors, specifically to an anti-malignant tumor agent which contains, as an active ingredient, a substance targeting ribosomal proteins showing increased expression in a malignant tumor cell.

First, the circumstances leading to the present invention will be explained before the explanation of the contents of the present invention. As shown in the section of Background Art, although it is said that even healthy persons have thousands of malignant tumor (cancer) cells every day, everyone does not necessarily develop disease. Biological defense mechanisms which prevent onset of disease even if malignant tumor cells develop is considered to be intrinsically provided in a living body. For example, it has been reported that incidence of liver cancer in autoimmune hepatitis (AIH) is about 0.7%/year (Aliment Pharmacol Ther 2006; 24:1197) and is obviously lower than 3%/year in chronic hepatitis C (Ann Intern Med 1999; 131:174). Here, it is considered that there are certain defense mechanisms leading up to canceration in autoimmune hepatitis (AIH) and the mechanisms effectively act. Thus, the inventors obtained approval from ethics committee and carried out analysis for identifying an antigen corresponding to an autoantibody existing in serum of patients with autoimmune hepatitis. First, serum antibodies of patients with autoimmune hepatitis, that is, immunoglobulins (hereinafter, simply called "IgG") were adsorbed and eluted by using protein G, and purified. When the purified IgG-containing solution (hereinafter, referred to as "purified IgG solution") was added to an in-vitro culture system of a malignant tumor cell strain, it was confirmed that in relation to the purified IgG solutions derived from serum of the patients with autoimmune hepatitis, some cases showed growth inhibition of the malignant tumor cells and the other cases showed no growth inhibition. Therefore, an antigen-antibody complex was formed by the reaction between an extract of the malignant tumor cell membrane protein and the serum IgG of each patient, the IgG was adsorbed to the protein G from the reaction solution, and the protein after adsorption was eluted. The difference of antiproliferative effects on the malignant tumor cell strain and the eluted proteins were analyzed by a mass spectrometer (LC/MS) and thus proteins showing increased expression in the malignant tumor cell were confirmed. As a result, RPL29 (Ribosomal Protein L29) and RPS4X (Ribosomal protein S4, X-linked) were detected as proteins showing increased expression in the malignant tumor cell. Both RPL29 and RPS4X are ribosomal proteins, and are common in that they are ribosomal proteins showing increased expression in the malignant tumor cell. More information will be explained in Reference Examples below.

In the ribosome which is a main body of an intracellular protein translator which includes 3 to 4 kinds of RNAs (ribonucleic acid) and 50 kinds or more of ribosomal proteins, the RNAs and the proteins cooperatively work. The ribosomal RNAs (rRNA) account for about two thirds of the total molecular weight of the ribosome, and the proteins account for the remaining one third. The ribosome is composed of two large and small subunits, the small subunit is responsible for decryption of codes, and the large subunit is responsible for elongation reaction of peptide chains. The ribosomal protein constituting the protein translator is a protein of very ancient origin in evolutionary history, and is considered to play a role in construction and protection of a three dimensional structure of rRNA and to assist the rRNA to express the enzymatic activities. Furthermore, some ribosomal proteins are known to control the expression at the time of the translation by binding to messenger RNAs (mRNA). That is, the ribosomal proteins are proteins which have been involved in the translation and the control which form the basis of life phenomenon, while keeping close contact with the RNAs.

The anti-malignant tumor agent of the present invention contains, as an active ingredient, a substance targeting ribosomal proteins showing increased expression in a malignant tumor cell. The "substance targeting ribosomal proteins" contained in the anti-malignant tumor agent of the present invention may be a substance involved in one of biological defense mechanisms which are considered to be intrinsically provided in a living body and which prevents onset of disease even if malignant tumor cells develop. Since the active ingredient is a substance involved in one of biological defense mechanisms which are considered to be intrinsically provided in a living body and which prevents onset of disease, the agent is a drug having high safety, can be used as a therapeutic and/or prophylactic agent for various malignant tumors, and is useful. The "substance targeting ribosomal proteins" contained in the anti-malignant tumor agent of the present invention acts as a proliferation inhibitor for various malignant tumor (cancer) cells. The manufacturing method of the "substance targeting ribosomal proteins" in the present invention is not particularly limited, and thus it may be a well-known method per se or a novel method which will be developed in the future.

In the present invention, the "substance targeting ribosomal proteins" showing increased expression in a malignant tumor cell may include (1) antibodies against respective substances, (2) a substance capable of activating or enhancing antibodies existing in a living body among the antibodies against the respective substances, (3) a substance capable of inducing production of antibodies against respective substances in the living body, or (4) antagonists against the respective substances.

In the present invention, substances capable of targeting the "ribosomal proteins showing increased expression in malignant tumor cells, RPL29 and/or RPS4X" include (1) an anti-RPL29 antibody and/or anti-RPS4X antibody as antibodies against respective substances, (2) an immunostimulator as a substance capable of activating or enhancing the anti-RPL29 antibody and/or anti-RPS4X antibody in a living body, and furthermore, (3) a vaccine as a substance capable of inducing production of antibodies against RPL29 and/or RPS4X in the living body. In the same way, (4) antagonists against respective substances include antagonists against RPL29 and/or RPS4X.

In the present invention, the "anti-RPL29 antibody" is preferably an antibody capable of binding to RPL29, and may be a monoclonal antibody or a polyclonal antibody. In addition, types of the antibodies may be a partial peptide such as Fab capable of antigen-antibody reaction, preferably include an intact-type antibody. In the same way, the "anti-RPS4X antibody" is preferably an antibody capable of binding to RPS4X, and may be a monoclonal antibody or a polyclonal antibody. In relation to the antibodies, types of the antibodies may be a partial peptide such as Fab capable of antigen-antibody reaction, preferably include an intact-type antibody. The antibody as the active ingredient contained in the anti-malignant tumor agent of the present invention is preferably an intact-type antibody capable of usually existing in a living body, because the antibody is considered to contain, as an active ingredient, a component provided in a living body of a healthy person who does not develop cancers easily, as a biological defense mechanism for preventing onset of disease even if malignant tumor cells develop.

The antibody against each of the above-mentioned substances can be manufactured by a well-known method per se. A starting material may be a derived from natural product material, or may be in accordance with a procedure such as gene recombination. The antibody can be produced using a sampled biological component as a raw material. The sampled biological component may be any biological component capable of producing the anti-RPL29 and/or -RPS4X antibody and is not particularly limited. In the present invention, the biological component is not particularly limited as long as it is a biological component containing the above-mentioned antibody, and is broadly exemplified by blood such as plasma and serum; spinal fluid; lymph; urine; tear; milk, and the like. Preferable biological components may include blood components such as plasma and serum; components including antibody-producing cells, and the like. For example, the biological component may be an auto-biological component of a person to whom the anti-malignant tumor agent of the present invention is administered, or a biological component of another person. For example, when the antibody is a monoclonal antibody, antibody-producing cells are collected from the sampled biological component, an antibody-producing hybridoma can be produced by a conventional method and thus an antibody can be produced. The antibody-producing cell in a living body may include, for example, a B cell and a plasmacyte. A partner cell in producing the hybridoma may be any cell which can be fused with the antibody-producing cell and which allows proliferation of the cell, and can include a well-known cell per se or a cell which will be developed in the future. For example, when the anti-RPL29 antibody and/or anti-RPS4X antibody are produced, they can be produced by selecting a cell capable of producing the anti-RPL29 antibody and/or anti-RPS4X antibody in the above-mentioned procedure. In addition, antibody components are separated and purified particularly from serum components among the biological components obtained by blood collection, and thus the anti-malignant tumor agent of the present invention containing a high-titer anti-RPL29 polyclonal antibody and/or anti-RPS4X polyclonal antibody can be manufactured. Furthermore, the biological component may be a malignant tumor cell (tumor cell collected from a cultured cell or a patient). An antibody can be manufactured by a well-known method per se by purification of the RPL29 or RPS4X from the malignant tumor cell and by the use as an antigen.

In the present invention, the "immunostimulator against the anti-RPL29 antibody and/or anti-RPS4X antibody" may be any substance which can further activate or enhance antibodies provided in a living body of a healthy person who does not develop cancers easily, as a biological defense mechanism for preventing onset of disease even if malignant tumor (cancer) cells develop. The immunostimulator against the anti-RPL29 antibody and/or anti-RPS4X antibody in a living body includes, for example, activators for antibody-producing cells in the living body such as IL-4, IL-5, IL-6, IL-10, IL-13, GM-CSF, TNF-α, bacteria and their bacterial cell components, polysaccharide of plant and fungus, nucleic acid, lipid-soluble vitamin, and mineral oil. The antibody-producing cell includes, for example, a B cell and a plasmacyte. The immunostimulators can be manufactured by well-known method per se or any methods which will be developed in the future. The IL-4, IL-5, IL-6, IL-10, IL-13, GM-CSF, TNF-α, bacteria and their bacterial cell components, polysaccharide of plant and fungus, nucleic acid, lipid-soluble vitamin, mineral oil, and the like may be derived from natural product, and also can be manufactured by a procedure of gene recombination or chemosynthesis.

In the present invention, it is sufficient that the "vaccine" as a substance capable of inducing production of antibody against RPL29 and/or RPS4X in a living body has antigenicity capable of producing the anti-RPL29 antibody and/or anti-RPS4X antibody having the same action as the antibody provided in a living body of a healthy person who does not develop cancers easily, as a biological defense mechanism for preventing onset of disease even if malignant tumor (cancer) cells are generated. Such a molecular includes RPL29 and/or RPS4X molecules themselves, partial peptides of these molecules, or the like. The vaccines can be manufactured by a well-known method per se or any methods which will be developed in the future. For example, RPL29 and/or RPS4X molecule themselves, partial peptides of these molecules or the like may be produced by a procedure of gene recombination, and can be produced by peptide synthesis.

Furthermore, an antagonist against the RPL29 and/or RPS4X includes an antagonistic drug, an antagonist, an antisubstance, a blocking drug, a blocker, and the like against the RPL29 and/or RPS4X. The antagonist may be a substance which directly acts on the RPL29 or RPS4X, and also be a substance which can inhibit the RPL29 or RPS4X by interacting with an RPL29 or RPS4X receptor.

The anti-malignant tumor agent of the present invention can contain a pharmaceutically acceptable carrier. The pharmaceutically acceptable carrier used for the above-mentioned anti-malignant tumor agent can include, for example, excipient, disintegrator or disintegrator aid, binder, lubricant, coating agent, dye, diluent, base, solubilizer or solubilizer aid, isotonizing agent, pH regulator, stabilizer, propellant, sticker, and the like.

As dosage forms of the anti-malignant tumor agent of the present invention, the agent may be locally or systemically administered. The preparation for parenteral administration may contain a sterilized aqueous or non-aqueous solution, suspension and emulsion. Examples of non-aqueous diluents include propylene glycol, polyethylene glycol, vegetable oil such as olive oil, and organic ester composition such as ethyl oleate, and these are suitable for injection. An aqueous carrier may contain water, alcoholic aqueous solution, emulsion, suspension, salt water and buffer medium. A parenteral carrier may contain a sodium chloride solution, Ringer dextrose, dextrose together with sodium chloride, and lactated Ringer together with a binder oil. The intravenous carrier may contain, for example, a filler for liquid, nutrients and electrolytes (e.g. based on Ringer dextrose). Furthermore, the anti-malignant tumor agent of the present invention may contain a preservative and other additives such as an antimicrobial compound, an antioxidant, a chelating agent, an inactivated gas, and the like.

Diseases on which the anti-malignant tumor agent of the present invention acts may be anymalignant tumors on which a substance targeting ribosomal proteins as an active ingredient contained in the anti-malignant tumor agent of the present invention prophylactically and/or therapeutically can act, and are not particularly limited. The malignant tumor is one or a plurality of cancers selected from liver cancer, pancreas cancer, breast cancer, large intestine cancer, non-small cell lung cancer, small cell lung cancer, prostate cancer, gastric cancer, thyroid cancer, ovarian cancer, salivary gland adenoid cystic carcinoma, acute myeloid leukemia, acute lymphocytic leukemia, chronic lymphocytic leukemia, chronic myeloid leukemia, malignant lymphoma, myxoid liposarcoma, glioblastoma, alveolar rhabdomyosarcoma, Wilms tumor, oligodendroglioma, adrenocortical carcinoma, multiple myeloma, medulloblastoma, endometrial cancer, esophageal cancer and Ewing's sarcoma. The malignant tumors are preferably liver cancer, pancreas cancer, breast cancer, large intestine cancer, non-small cell lung cancer, small cell lung cancer and prostate cancer; and liver cancer and pancreas cancer are particularly preferable.

The antibody against the ribosomal protein showing increased expression in malignant tumor cells, specifically anti-RPL29 antibody and/or anti-RPS4X antibody is to intrinsically exist in a living body. The antibody against the ribosomal protein showing increased expression in malignant tumor cells, specifically anti-RPL29 antibody and/or anti-RPS4X antibody seems to be able to maintain a state that is considered to be one of biological defense mechanisms which prevent onset of disease even if malignant tumor cells develop, and although thousands of malignant tumor (cancer) cells are caused every day, a state where cancer does not develop easily is considered to be able to be maintained.

Therefore, in the prevent invention, it is considered that development of malignant tumor and prognosis after the development can also be predicted by measuring the anti-RPL29 antibody and/or anti-RPS4X antibody in the living body. Preferably, each antibody is quantitatively examined, specifically by measuring the anti-RPL29 antibody titer and/or anti-RPS4X antibody titer in the biospecimen. The present invention extends also to an examination method of malignant tumors which characteristically uses anti-RPL29 antibody titer and/or anti-RPS4X titer in the biospecimen, as an indicator. In the present invention, the biospecimen may be any biospecimen which has a possibility of containing the above-mentioned antibody, and is not particularly limited. The biospecimen is broadly exemplified by blood such as plasma and serum; spinal fluid; lymph; urine; tear; milk; and the like. Preferable biospecimen may include blood components such as plasma and serum. The measurement method for the antibody titer can be based on a well-known method per se or a method which will be developed in the future. For example, serial serum dilution, fixed-concentration serum dilution, and the like can be applied. Specifically, enzyme-linked immunosorbent assay (ELISA), radioimmune assay (RIA), chemiluminescent immunoassay (CLIA), latex agglutination nephelometry (LA), and the like can be applied. The examination of the malignant tumor in the present invention can be carried out particularly preferably for predicting prognosis of the malignant tumor. A patient with high anti-RPL29 and/or -RPS4X antibody titer is considered to have a good prognosis, a low recurrence rate and a high survival rate. Here, a cut-off value of each antibody titer can be determined by an examination procedure, a testing equipment, and the like. For example, when the value is measured by the ELISA method in accordance with the method of the Examples mentioned later, an absorbance at 405 nm can be 0.3 to 0.7 $OD_{405\ nm}$, preferably 0.5 $OD_{405\ nm}$. Meanwhile, since an absorbance at a particular wavelength varies depending on measurement conditions and measurement equipment, an appropriate cut-off value is required to be determined in a case where the examination method is generalized.

As types of the malignant tumors applicable to the examination method, there can be applied one or a plurality of cancers selected from liver cancer, pancreas cancer, breast cancer, large intestine cancer, non-small cell lung cancer, small cell lung cancer, prostate cancer, gastric cancer, thyroid cancer, ovarian cancer, salivary gland adenoid cystic carcinoma, acute myeloid leukemia, acute lymphocytic leukemia, chronic lymphocytic leukemia, chronic myeloid leukemia, malignant lymphoma, myxoid liposarcoma, glioblastoma, alveolar rhabdomyosarcoma, Wilms tumor, oligodendroglioma, adrenocortical carcinoma, multiple myeloma, medulloblastoma, endometrial cancer, esophageal cancer and Ewing's sarcoma. Liver cancer, pancreas cancer, breast cancer, large intestine cancer, non-small cell lung cancer, small cell lung cancer and prostate cancer are preferable, and liver cancer and pancreas cancer are particularly preferable.

EXAMPLES

The present invention will be specifically explained by reference to Reference Examples and Examples in order to promote a further understanding of the present invention, but it is needless to say that the present invention is not limited to these examples. In Reference Examples, the study process leading to the completion of the present invention will be shown. This study using the following clinical specimen is approved from ethics committee in Okayama University.

(Reference Example 1) Examination of the Antiproliferative Effects of the Serum IgG on Liver Cancer Cell Strain Huh7

In this Reference Example, the antiproliferative effects of the serum IgG on liver cancer cell strain Huh7 were examined.

The Huh 7 was adjusted to be $5.0 \times 10^4$ cell/ml, and then was inoculated on a 96 well plate for cell culture at 100 μl/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma chemical, MO)+1% sodium pyruvate (Sigma-Aldrich Co., St. Louis, Mo.)+1% penicillin-streptomycin solution (Sigma-Aldrich Co.).

After the approval from the ethics committee, analysis for identifying an antigen corresponding to an autoantibody in serum of patients with autoimmune hepatitis (AIH) was carried out. First, by adding a protein G (Invitrogen Dynal AS, Oslo, Norway) as an affinity support for antibody purification to serum samples obtained from the AIH patients (Case 1, Case 2), nonspecifically adsorbing IgG in serum to the resultant substance, washing the protein G through the use of a washing liquid (0.1 M Na-Phosphate Buffer, pH 7.4), and eluting the protein adsorbed to the protein G through the use of an eluate (50 mM Glycine Buffer, pH 2.8), there was obtained a solution (purified IgG solution) containing 0.25-0.5 μg/μl of IgG extracted from serum of the AIH patients.

Twenty four hours after the start of the culture, 1 μg of IgG extracted from serum of the AIH patient was added to each well, and the resultant substance was adjusted to be 10 μg/ml. As a control, only the same amount of eluate (50 mM Glycine Buffer, pH 2.8) was added. Forty two hours after the start of the culture, [methyl-$^3$H]-thymidine (TRK637; GE Healthcare Amersham Biosciences, Buckinghamshire, UK) was added to each well, and proliferation of Huh7 was confirmed. Forty eight hours after the start of the culture, the proliferation was measured by a liquid scintillation counter, and the measurement results were indicated by ratios to a control. As a result, in the AIH Case 1, growth inhibition of Huh7 was observed (see FIG. 1). As shown in the result, it is considered that there exist some cases of having IgG which inhibits the growth of Huh7 in serum of the AIH patients.

(Reference Example 2) Regarding an Antigen Corresponding to IgG Inhibiting the Growth of the Liver Cancer Cell Strain Hu7

In this Reference Example, an antigen corresponding to IgG inhibiting the growth of Huh7 confirmed in Reference Example 1 was analyzed.

1) A membrane protein was extracted from Huh7 through the use of ProteoJET™ Membrane Protein Extraction Kit (Thermo Fischer Scientific Inc., IL, USA).

2) The protein G (Invitrogen Dynal AS, Oslo, Norway) as an affinity support for purifying the antibody was added to the serum sample obtained from each AIH patient (Case 1, Case 2) in Reference Example 1, and the serum IgG was nonspecifically adsorbed to the resultant substance.

3) The protein G was washed by 0.1 M of Na-Phosphate Buffer, pH 7.4, was then added to a solution containing a membrane protein extract of Huh7 as an antigen and was treated at room temperature for 1 hour, and thus the serum IgG adsorbed nonspecifically to the protein G was caused to react with the antigen. When there is an antibody against the membrane protein in serum, the reaction between the antibody and an antigen is generated, resulting in formation of an antigen-antibody complex.

4) The resultant substance was washed with 0.1 M Na-Phosphate Buffer, pH 7.4, then the protein adsorbed to the protein G was eluted with an eluate (50 mM Glycine Buffer, pH 2.8), the eluted protein was trypsin-digested by using ProteoExtract™ All-in-One Trypsin Digestion Kit (Calbiochem, Darmstadt, Germany) and was measured by a mass spectrometer (LC/MS). The measured results were searched by a database Swiss-Prot.

Their results are shown in Tables 1 and 2. The results showed a possibility that the antigens corresponding to IgG existing in serum of AIH patients and showing antiproliferative effects on Huh7 were RPL29 (Ribosomal protein L29) and RPS4X (Ribosomal protein S4, X-Linked).

TABLE 1

| Proteins searched by Swiss-Prot (AIH CASE 1) | |
|---|---|
| HUMAN Ig gamma-1 chain C region | HUMAN Ig heavy chain V-III region BUT |
| HUMAN Ig gamma-3 chain C region | HUMAN Ig heavy chain V-III region WEA |
| HUMAN Ig gamma-2 chain C region | HUMAN Ig kappa chain V-IV region Len |
| HUMAN Ig gamma-4 chain C region | HUMAN Ig heavy chain V-III region WAS |
| HUMAN Ig kappa chain C region | HUMAN Ig heavy chain V-III region POM |
| HUMAN Ig lambda chain C regions | HUMAN Ig heavy chain V-III region TUR |
| HUMAN Complement C1q subcomponent subunit C | HUMAN Ig heavy chain V-III region TIL |
| HUMAN Ig kappa chain V-III region VG (Fragment) | HUMAN Ig heavy chain V-I region HG3 |
| HUMAN Ig kappa chain V-III region SIE | HUMAN Complement C1q subcomponent subunit B |
| HUMAN Ig kappa chain V-III region WOL | HUMAN Ig heavy chain V-II region ARH-77 |
| HUMAN Ig kappa chain V-III region HAH | HUMAN Ig heavy chain V-II region NEWM |
| HUMAN Ig kappa chain V-III region HIC | HUMAN Ig lambda chain V-IV region Hil |
| HUMAN Ig kappa chain V-III region GOL | HUMAN Ig heavy chain V-III region HIL |
| HUMAN Ig kappa chain V-III region Ti | HUMAN Ig heavy chain V-I region SIE |
| HUMAN Ig kappa chain V-II region TEW | HUMAN Ig heavy chain V-I region Mot |
| HUMAN Ig kappa chain V-II region Cum | HUMAN Ig heavy chain V-I region EU |
| HUMAN Ig kappa chain V-II region GM607 (Fragment) | HUMAN 40S ribosomal protein S4, X isoform |
| HUMAN Complement C1q subcomponent subunit A | HUMAN 60S ribosomal protein L29 |
| HUMAN Ig heavy chain V-III region BRO | HUMAN Ig lambda chain V-III region SH |
| HUMAN Ig heavy chain V-III region TEI | |

TABLE 2

| Proteins searched by Swiss-Prot (AIH CASE 2) | |
|---|---|
| HUMAN Ig gamma-3 chain C region | HUMAN Ig kappa chain V-IV region Len |
| HUMAN Ig gamma-1 chain C region | HUMAN Ig heavy chain V-III region GAL |
| HUMAN Ig gamma-2 chain C region | HUMAN Ig heavy chain V-III region WAS |
| HUMAN Ig gamma-4 chain C region | HUMAN Ig heavy chain V-III region POM |
| HUMAN Ig lambda chain C regions | HUMAN Ig heavy chain V-III region TUR |
| HUMAN Ig kappa chain C region | HUMAN Ig heavy chain V-III region TIL |
| HUMAN Complement C1q subcomponent subunit B | HUMAN Ig kappa chain V-I region WEA |
| HUMAN Complement C1q subcomponent subunit C | HUMAN Ig kappa chain V-I region WAT |
| HUMAN Ig kappa chain V-III region SIE | HUMAN Ig kappa chain V-I region Hau |
| HUMAN Ig kappa chain V-III region WOL | HUMAN Ig kappa chain V-II region RPMI 6410 |

TABLE 2-continued

Proteins searched by Swiss-Prot (AIH CASE 2)

Figure 2:
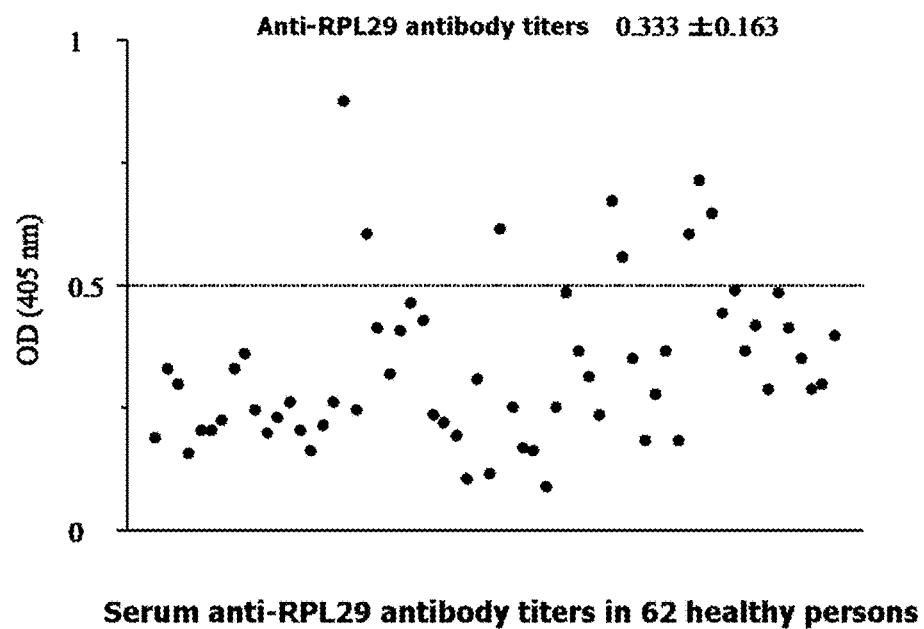
FIG. 2 A diagram showing anti-RPL antibody titers on each serum derived from healthy persons (62 cases) (Reference Example 3).

HUMAN Ig kappa chain V-III region HAH
HUMAN Ig kappa chain V-III region HIC
HUMAN Ig kappa chain V-III region GOL
HUMAN Ig kappa chain V-III region Ti
HUMAN Ig kappa chain V-II region TEW
HUMAN Ig kappa chain V-II region Cum
HUMAN Ig kappa chain V-II region GM607
HUMAN Ig heavy chain V-III region BRO
HUMAN Ig heavy chain V-III region BUT
HUMAN Ig heavy chain V-III region WEA
HUMAN Ig heavy chain V-III region TEI
HUMAN Complement C1q subcomponent subunit A
HUMAN Ig kappa chain V-I region EU
HUMAN Ig lambda chain V-IV region Hil
HUMAN Ig kappa chain V-III region VG
HUMAN Ig heavy chain V-II region ARH-77
HUMAN Ig heavy chain V-II region NEWM
HUMAN Ig heavy chain V-III region HIL
HUMAN Ig lambda chain V-III region LOI
HUMAN Ig heavy chain V-I region V35
HUMAN Ig lambda chain V-III region SH
HUMAN Ig heavy chain V-I region SIE
HUMAN Ig heavy chain V-I region Mot
HUMAN Ig heavy chain V-I region EU (Reference Example 3) Examination of the Serum Anti-RPL29 Antibody Titer In this Example, as to serum of 62 healthy persons (FIG. 2) and 52 AIH patients (FIG. 3), the serum anti-RPL29 antibody titers were measured, and tendency of the anti-RPL29 antibody titers in each group was confirmed.

The antibody titers were measured by the following ELISA method.

1) 1 μg/ml Recombinant RPL29 (H00006259-P01: Avnova, Taipei, Taiwan) was added in an amount of 100 μl to each well of 96 well microplate, and was left to stand for 1 hour and the antigen was solidified.

2) 1% bovine serum albumin was added in an amount of 300 μl/well, and after being subjected to blocking processing for 15 minutes, a serum solution obtained by diluting each serum of the healthy persons or the AIH patients by 100 times was added in an amount of 100 μl/well and was caused to react for 1 hour.

3) After washing, 1 μg/ml HRP-labeled anti-human IgG antibody was added in an amount of 100 μl/well and was caused to react for 1 hour.

4) After further washing, 2,2'-azino-bis[3-ethylbenzothiazoline-6-sulfonate] was added in an amount of 100 μl/well, and was caused to sufficiently react.

5) The absorbance at 405 nm was measured by an ELISA reader (Model 680 Microplate Reader: Bio-Rad Laboratories Ltd., Tokyo, Japan). The AIH patient (Case 1) serum shown in Reference Example 1 was used as a positive control, and a diluted solution of serum was used for a negative control, instead of serum. After the measurement of the absorbance, the absorbance of the negative control was deducted from the measured absorbance, and the obtained value was defined as the anti-RPL29 antibody titer.

Figure 3:
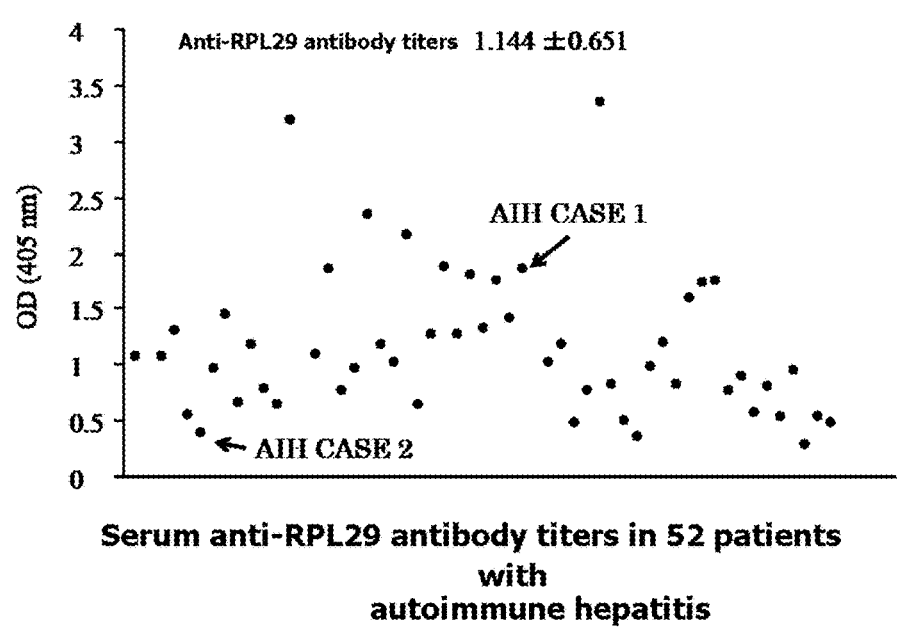
FIG. 3 A diagram showing anti-RPL antibody titers on each serum derived from AIH patients (52 cases) (Reference Example 3).

Although the serum anti-RPL29 antibody titers in the AIH patients varied depending on the cases, Case 1 with inhibited proliferation of Huh7 in Reference Example 1 exhibited a relatively high anti-RPL29 antibody titer of 1.8465 $OD_{405\ nm}$ (see FIG. 3). Meanwhile, Case 2 without inhibited proliferation of the Huh7 cells showed a relatively low anti-RPL29 antibody titer of 0.369 $OD_{405\ nm}$ (see FIG. 3). Although the anti-RPL29 antibody is contained also in serum of healthy persons, their antibody titers were generally lower than those in cases with autoimmune hepatitis ($P<0.0001$). In addition, 87% of healthy persons showed the antibody titers of less than 0.5 $OD_{405\ nm}$ (see FIG. 2).

(Reference Example 4) Confirmation of Expressions of the RPL29 and RPS4X in Human Liver Cancer Cell Strains Each of cell strains (Huh7, PLC/PRF/5, Hep3B, HepG2, HLE, HLF, and SK-Hep-1) which are human liver cancer cell strains was inoculated on a 6 well plate for cell culture at 2 ml/well. The culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma chemical, MO)+1% sodium pyruvate (Sigma-Aldrich Co., St. Louis, Mo.)+1% penicillin-streptomycin solution (Sigma-Aldrich Co.). At the time when the cells became 80% confluent, the culture solution was removed, and 400 μl of Pierce IP Lysis Buffer (Thermo Fisher Scientific Inc., IL) was added to each well. After a 15-minute stirring, the cells were crushed by a bead crusher (TAITEC, Saitama, Japan) and were then centrifuged at 13,000 g for 10 minutes, and thus a supernatant was collected. Proteins were extracted by addition of an equivalent amount of 2×sample buffer (20% of glycerol, 4% of SDS, 125 mM of Tris-HCl/pH6.8, 10% of mercaptoethanol, 0.004% of bromophenol blue (BPB)) to the resulting supernatant and by boiling for 5 minutes.

The proteins extracted from various human liver cancer cell strains were electrophoresed by SDS-PAGE according to a conventional method. The electrophoresed proteins were blotted on a PVDF membrane according to a conventional method. This was subjected to blocking processing for 1 hour with PVDF Blocking Reagent for Can Get Signal (TOYOBO, Osaka, Japan) and the resultant substance was then treated for 1 hour with a mouse anti-RPL29 antibody (H00006259-B02P: Avnova, Taipei, Taiwan) or anti-RPS4X antibody (PAB17574: Avnova, Taipei, Taiwan), and an anti-β-actin antibody (Sigma-Aldrich Co., Mo) as primary antibodies. The membrane was washed and was then caused to react for 1 hour an HRP-labeled anti-IgG antibody (RPN2124: GE Healthcare, UK) as a secondary antibody. After the washing, the membrane was colored with ECL Western Blotting Detection System (RPN2132: GE Healthcare, UK) and was detected by a luminometer.

Figure 4:
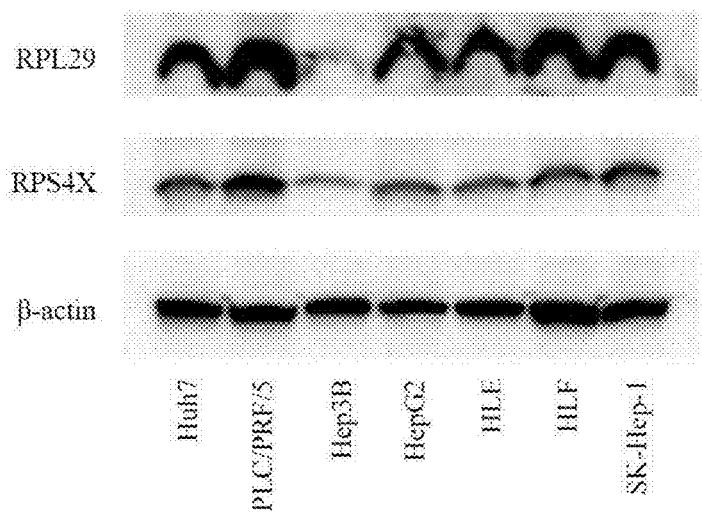
FIG. 4 Photographs confirming the expressions of RPL29 and RPS4X in various human liver cancer cell strains (Reference Example 4).

All of the seven human liver cancer cell strains used in the examination showed protein expressions of the RPL29 and RPS4X even if there are differences in degree (see FIG. 4).

(Reference Example 5) Confirmation of Expression of the RPL29 in Human Pancreas Cancer Cell Strains Each of the cell strain (ASPC-1, BxPC-3, PANC-1, MIA PaCa-2, KLM-1, Suit-2, and T3M4) which are human pancreas cancer cell strains was respectively cultured on a petri dish having a diameter of 10 cm. The culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma chemical, MO)+1% sodium pyruvate (Sigma-Aldrich Co., St. Louis, Mo.)+1% penicillin-streptomycin solution (Sigma-Aldrich Co.). At the time when the cells became 100% confluent, proteins were extracted by addition of 2×sample buffer (20% of glycerol, 4% of SDS, 125 mM of Tris-HCl/pH6.8, 10% of mercaptoethanol, 0.004% of bromophenol blue (BPB)), by collection of the cells through the use of a cell scraper, and by boiling for 5 minutes.

Figure 5:
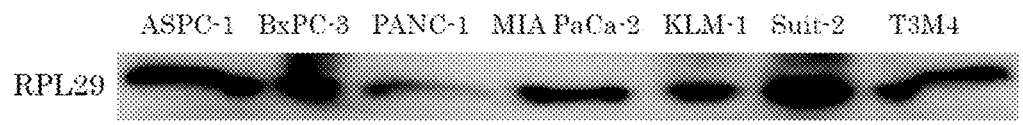
FIG. 5 A photograph confirming the expression of RPL29 in human pancreas cancer cell strain (Reference Example 5).

The proteins extracted from human pancreas cancer cell strains by the above-mentioned method were electrophoresed by SDS-PAGE according to a conventional method. The electrophoresed proteins were blotted on a polyvinylidene fluoride (PVDF) membrane according to a conventional method. This was subjected to blocking processing for 1 hour with PVDF Blocking Reagent for Can Get Signal (TOYOBO, Osaka, Japan) and the resultant substance was then treated for 1 hour with a mouse anti-RPL29 antibody (H00006159-B02P: Avnova, Taipei, Taiwan) as a primary antibody. The membrane was washed and was then caused to react for 1 hour with an HRP-labeled anti-mouse IgG antibody (RPN2124: GE Healthcare, UK) as a secondary antibody. After the washing, the membrane was colored with ECL Western Blotting Detection System (RPN2132: GE Healthcare, UK), and was detected by a luminometer. As a result, all of seven human pancreas cancer cell strains used in the examination showed expression of the RPL29 (see FIG. 5).

(Reference Examination 6) Intracellular Signal Change of the Liver Cancer Cell Strain Huh7 by the Serum IgG The liver cancer cell strain Huh7 was adjusted to be $5.0\times10^4$ cell/ml, and was then inoculated on a 6 well plate for cell culture at 2 ml/well. Meanwhile, the culture solution was cultured at 37° C. under 5% $CO_2$ through the use of DMEM (Invitrogen Co., Carlsbad, Calid.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO).

Twelve hours after the start of the culture, 10 µg of IgG extracted from serum of the AIH patients or healthy persons by the same procedure as in Reference Example 1 was added to each well (5 µg/ml). As a control, only the same amount of eluate (50 mM Glycine Buffer, pH 2.8) was added. Twenty four hours after the start of the culture, the culture solution was removed, and 400 µl of Pierce IP Lysis Buffer (Thermo Fisher Scientific Inc., IL) was added to each well. After a 15-minute stirring, the cells were crushed by a bead crusher (TAITEC, Saitama, Japan), and were then centrifuged at 13,000 g for 10 minutes, and thus a supernatant was collected. Proteins were extracted by addition of an equivalent amount of 2×sample buffer (20% of glycerol, 4% of SDS, 125 mM of Tris-HCl/pH6.8, 10% of mercaptoethanol, 0.004% of bromophenol blue (BPB)) to the resulting supernatant and by boiling for 5 minutes.

The proteins extracted from Huh7 stimulated by human IgG in the above-mentioned method were electrophoresed by SDS-PAGE according to a conventional method. The electrophoresed proteins were blotted on a PVDF membrane according to a conventional method. This was subjected to blocking processing for 1 hour with PVDF Blocking Reagent for Can Get Signal (TOYOBO, Osaka, Japan) and the resultant substance was then treated for 1 hour with each primary antibody of β-catenin, Cyclin D1, p-mTOR (Ser2448) and p-p70 S6 Kinase (Thr389) (Cell signaling Technology, Inc., MA) or an anti-β-actin antibody (Sigma-Aldrich Co., MO). The membrane was washed and was then caused to react for 1 hour with an HRP-labeled anti-IgG antibody (RPN2124: GE Healthcare, UK) as a secondary antibody. After the washing, the membrane was then colored with ECL Western Blotting Detection System (RPN2132: GE Healthcare, UK) and was detected by a luminometer.

Figure 6:
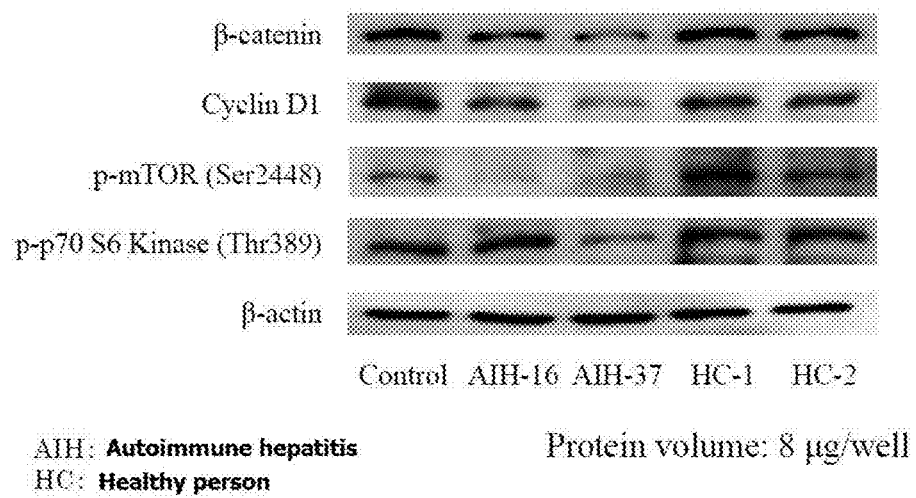
FIG. 6 Photographs confirming various intracellular signal changes in liver cancer cell strain Huh7 by a serum IgG (Reference Example 6).

There were some cases where decreased expression of intracellular β-catenin and Cyclin D1 and further decreased phosphorylation of m-TOR and downstream p70 S6 kinase in Huh7 were found by administering IgG extracted from serum of patients with autoimmune hepatitis in the same procedure as in Reference Example 1 (FIG. 6).

(Reference Example 7) Confirmation of Expression of the RPL29 and RPS4X in Various Human Malignant Tumor Cells Proteins were extracted from various human malignant tumor cell strains (large intestine cancer, small cell lung cancer, non-small cell lung cancer, breast cancer, prostate cancer, and pancreas cancer) in the same procedure as in Reference Example 5 and expressions of RPL29 and RPS4X were confirmed.

A large intestine cancer cell strain HCT15 or a small cell lung cancer cell strain H1048, a non-small cell lung cancer cell strain PC-9, abreast cancer cell strain MCF-7 and a prostate cancer cell strain PC-3 were inoculated on a dish having a diameter of 10 cm. Meanwhile, the culture solution was cultured at 37° C. under 5% $CO_2$ through the use of RPMI-1640 (Sigma-Aldrich Co., MO)+10% heat-inactivated FBS (Vitromex, Vilshofen, Germany)+1% penicillin-streptomycin solution (Sigma-Aldrich Co., MO). In the same way, a pancreas cancer cell strains AsPC-1 and Panc-1 were cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). At the time when the cells became 80% confluent, 2×sample buffer (20% of Glycerol, 4% of SDS, 125 mM of Tris-HCl/pH6.8, 10% of mercaptoethanol, 0.004% of BPB) was added, the cells were collected by a cell scraper and were boiled for 5 minutes.

The proteins extracted from various human malignant tumor cell strains (large intestine cancer, small cell lung cancer, non-small cell lung cancer, breast cancer, prostate cancer, and pancreas cancer) were electrophoresed by SDS-PAGE according to a conventional method. The electrophoresed proteins were blotted on a PVDF membrane according to a conventional method. This was subjected to blocking processing for 1 hour with PVDF Blocking Reagent for Can Get Signal (TOYOBO, Osaka, Japan) and the resultant substance was then treated for 1 hour with a mouse anti-RPL29 antibody (H00006259-B02P: Avnova, Taipei, Taiwan) or anti-RPS4X antibody (PAB17574: Avnova, Taipei, Taiwan), and an anti-β-actin antibody (Sigma-Aldrich Co., Mo) as primary antibodies. The membrane was then caused to react for 1 hour with an HRP-labeled anti-IgG antibody (RPN2124: GE Healthcare, UK) as a secondary antibody. After the washing, the membrane was then colored with ECL Western Blotting Detection System (RPN2132: GE Healthcare, UK) and was detected by a luminometer.

Figure 7:
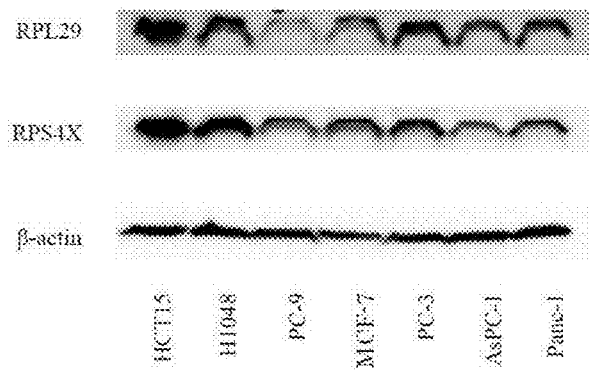
FIG. 7 Photographs confirming expressions of RPL29 and RPS4X in human various malignant tumor cell strains (Reference Example 7).

The various human malignant tumor cell strains (large intestine cancer, small cell lung cancer, non-small cell lung cancer, breast cancer, prostate cancer, and pancreas cancer) used in the examination showed protein expressions of the RPL29 and RPS4X even if there are differences in degree (see FIG. 7).

(Example 1) Antiproliferative Effects of the Anti-RPL29 Antibody on Liver Cancer Cell Strain Huh7

A liver cancer cell strain Huh 7 was adjusted to be $5.0 \times 10^4$ cell/ml, and was then inoculated on a 96 well plate for cell culture at 100 μl/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twenty four hours after the start of the culture, 0 μg/ml, 1 μg/ml or 5 μg/ml of anti-RPL29 antibody (H00006159-B02P: Avnova, Taipei, Taiwan), and 0 μg/ml or 5 μg/ml of recombinant RPL29 (H00006259-P01: Avnova, Taipei, Taiwan) were added. Forty two hours after the start of the culture, [methyl-$^3$H]-thymidine (TRK637; GE Healthcare Amersham Biosciences, Buckinghamshire, UK) was added to each well, and forty eight hours after the start of the culture, was measured by a liquid scintillation counter, and cell proliferation was confirmed. The measurement results were represented by ratios to a control.

Figure 8:
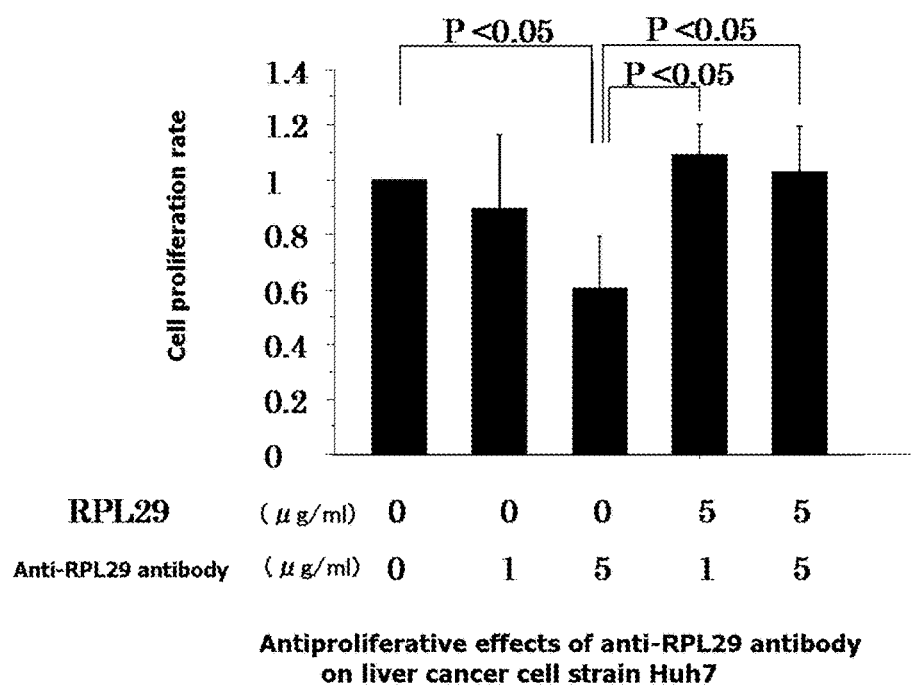
FIG. 8 A diagram showing antiproliferative effects of the anti-RPL29 antibody on liver cancer cell strain Huh7 (Example 1).

It was confirmed that the anti-RPL29 antibody inhibited proliferation of the Huh7 concentration-dependently. It was also observed that the antiproliferative effects of the anti-RPL29 antibody on the Huh7 were offset by adding the anti-RPL29 antibody and a recombinant RPL29. On the other hand, the proliferation of the Huh7 was not increased even by addition of an excessive recombinant RPL29 having a concentration capable of offsetting the action of the anti-RPL29 antibody, or more. These results suggested that the presence of the anti-RPL29 antibody was considered to be associated with the proliferation of the Huh7 (see FIG. 8).

(Example 2) Serum Anti-RPL29 Antibody in Patients with Unresectable Pancreas Cancer and their Prognoses In this Example, as to 39 patients, as a target, with unresectable progressive pancreas cancer who were diagnosed as pancreas cancer by cytodiagnosis or tissue diagnosis and who were at stage 4 in UICC classification (stage 4b in TNM classification), there were measured serum anti-RPL29 antibody titers before the onset of the treatment and there was analyzed the relationship with a time period from the onset of the treatment to death of the patient by Kaplan-meier method, and thus the serum anti-RPL29 antibody titer and possibility of prognosis prediction were examined. The serum anti-RPL29 antibody titers were measured by the same procedure as in Reference Example 3.

Figure 9:
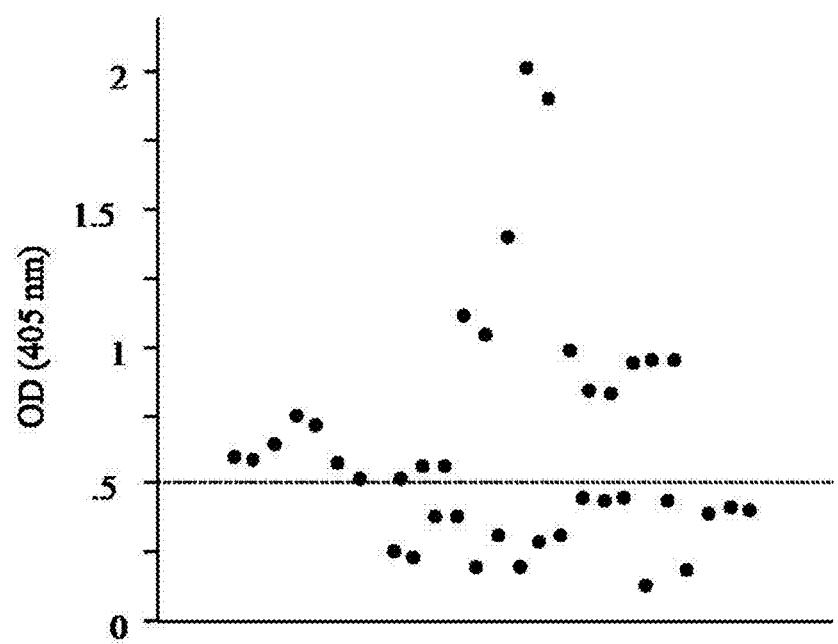
FIG. 9 A diagram showing serum anti-RPL29 antibody titers in patients with unresectable pancreas cancer (Example 2).
Figure 10:
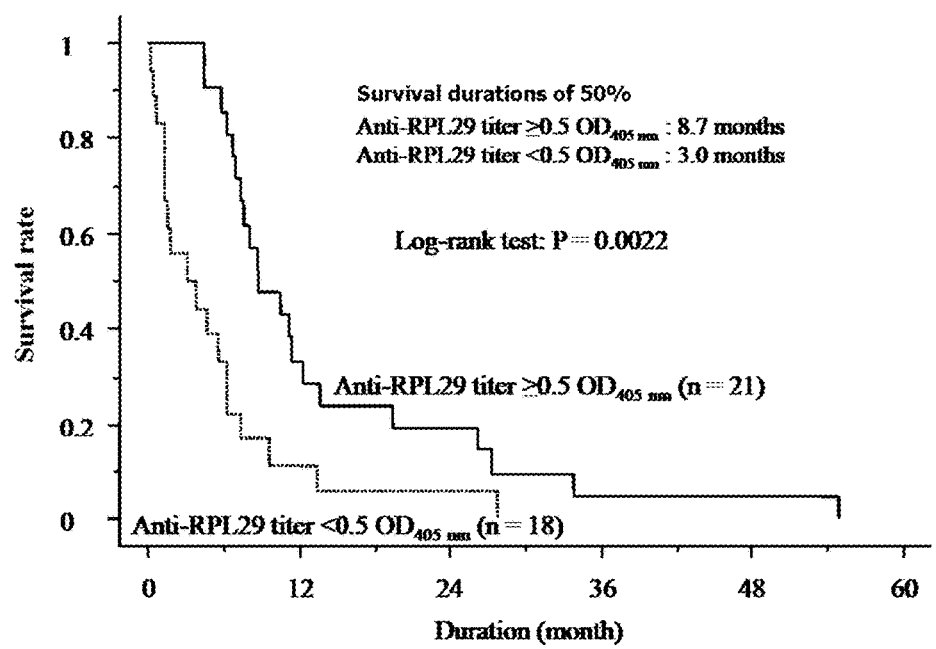
FIG. 10 A diagram showing a relationship between the serum anti-RPL29 antibody titers and the survival durations in patients with unresectable pancreas cancer (Example 2).

1) Target: 39 patients with unresectable progressive pancreas cancer who were diagnosed as pancreas cancer by cytodiagnosis or tissue diagnosis and who were at stage 4 in UICC classification (stage 4b in TNM classification) were targeted. Meanwhile, patients fell under ECOG Performance status 0, 1 or 2.
2) Treatment: 1000 mg/m$^2$ of gemcitabine was intravenously infused at Day 1, 8 and 15, with 4 weeks as one course.
3) Analysis: The serum anti-RPL29 antibody titers before treatment were measured in the same procedure as in Reference Example 3, and their relationship with a time period from the onset of the treatment to death of the patient was analyzed by Kaplan-meier method. The serum anti-RPL29 antibody titers of the respective patients are shown in FIG. 9, and their survival periods are shown in FIG. 10. Anti-RPL29 antibodies having various antibody titers were found in the serum of the patients with unresectable pancreas cancer. In the cases of the serum anti-RPL29 antibody titer of 0.5 $OD_{405\ nm}$ or more, the survival periods are clearly longer than those of the cases of less than 0.5 $OD_{405\ nm}$.

(Example 3) Antiproliferative Effects of the Anti-RPL29 Antibody on Liver Cancer Cell Strain PLC/PRF/5

A liver cancer cell strain PLC/PRF/5 was adjusted to be $5.0 \times 10^4$ cell/ml, and was then inoculated on a 96 well plate for cell culture at 100 μl/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, 0 μg/ml, 1 μg/ml or 5 μg/ml of anti-RPL29 antibody (H00006159-B02P: Avnova, Taipei, Taiwan), and 0 μg/ml or 5 μg/ml of recombinant RPL29 (H00006159-P01: Avnova, Taipei, Taiwan) were added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 11:
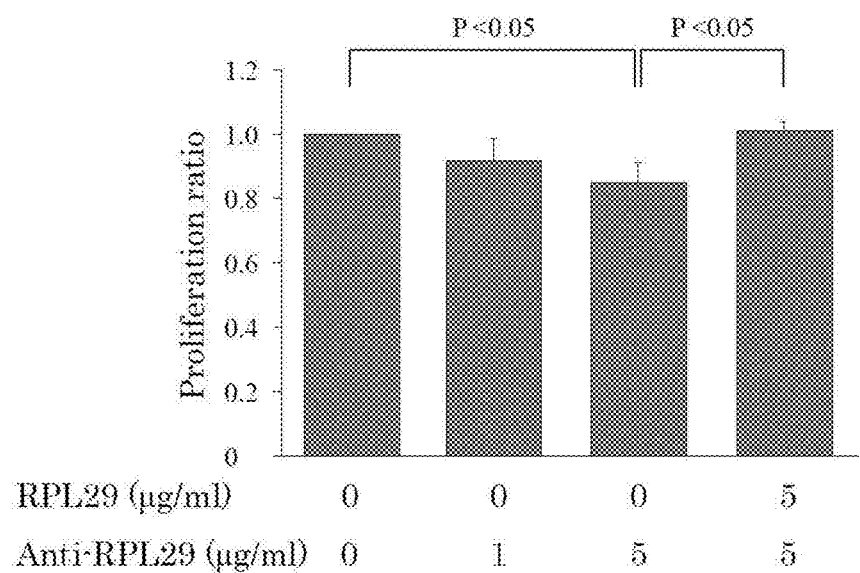
FIG. 11 A diagram showing antiproliferative effects of the anti-RPL29 antibody on liver cancer cell strain PLC/PRF/5 (Example 3).

The anti-RPL29 antibody inhibited cell proliferation of the liver cancer cell strain PLC/PRF/5 concentration-dependently. The antiproliferative effects of the anti-RPL29 antibody on the liver cancer cell strain PLC/PRF/5 were offset by adding the anti-RPL29 antibody and a recombinant RPL29 (see FIG. 11). Therefore, it was confirmed that the substance exhibiting the antiproliferative effects on the liver cancer cells was the anti-RPL29 antibody. Consequently, a high level of the anti-RPL29 antibody was found in a living body by administering the anti-RPL29 antibodies or by administering a substance capable of activating or enhancing the endogenous anti-RPL29 antibody existing in the living body and a substance capable of inducing production of the anti-RPL29 antibodies in the living body, and thus effective anti-tumor effects can be expected.

(Example 4) Intracellular Signal Change of Liver Cancer Cell Strain Huh7 by the Anti-RPL29 Antibody Liver cancer cell strain Huh7 was adjusted to be $5.0 \times 10^4$ cell/ml, and was then inoculated on a 6 well plate for cell culture at 2 ml/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, 0 μg/ml, 1 μg/ml or 5 μg/ml of anti-RPL29 antibody (H00006159-B02P: Avnova, Taipei, Taiwan) was added. Twenty four hours after the start of the culture, the culture solution was removed, and 400 μl of Pierce IP Lysis Buffer (Thermo Fisher Scientific Inc., IL) was added to each well. After a 15-minute stirring, the cells were crushed by a bead crusher (TAITEC, Saitama, Japan) and were then centrifuged at 13,000 g for 10 minutes, and thus a supernatant was collected. Proteins were extracted by addition of an equivalent amount of 2×sample buffer (20% of glycerol, 4% of SDS, 125 mM of Tris-HCl/pH6.8, 10% of mercaptoethanol, 0.004% of bromophenol blue (BPB)) to the resulting supernatant and by boiling for 5 minutes.

The proteins extracted, in the above-mentioned method, from Huh7 stimulated by the anti-RPL29 antibody (H00006159-B02P: Avnova, Taipei, Taiwan) were electrophoresed by SDS-PAGE according to a conventional method. The electrophoresed proteins were blotted on a PVDF membrane according to a conventional method. This was subjected to blocking processing for 1 hour with PVDF Blocking Reagent for Can Get Signal (TOYOBO, Osaka, Japan) and the resultant substance was then treated for 1 hour with each primary antibody of Casein Kinase 1α, Axin1, Pan-GSK, p-GSK-3β (ser9), p-β-Catenin (Thr41/Ser45), β-Catenin, Cyclin D1, c-Jun, Met, Survivin, p-Tuberin/TSC2 (Thr1462), p-mTOR (Ser2448) and p-p70 S6 Kinase (Thr389) (Cell signaling Technology, Inc., MA) or an anti-β-actin antibody (Sigma-Aldrich Co., MO). The membrane was washed and was then caused to react for 1 hour with an HRP-labeled anti-IgG antibody (RPN2124: GE Healthcare, UK) as a secondary antibody. After the washing, the membrane was then colored with ECL Western Blotting Detection System (RPN2132: GE Healthcare, UK) and was detected by a luminometer.

Figure 12:
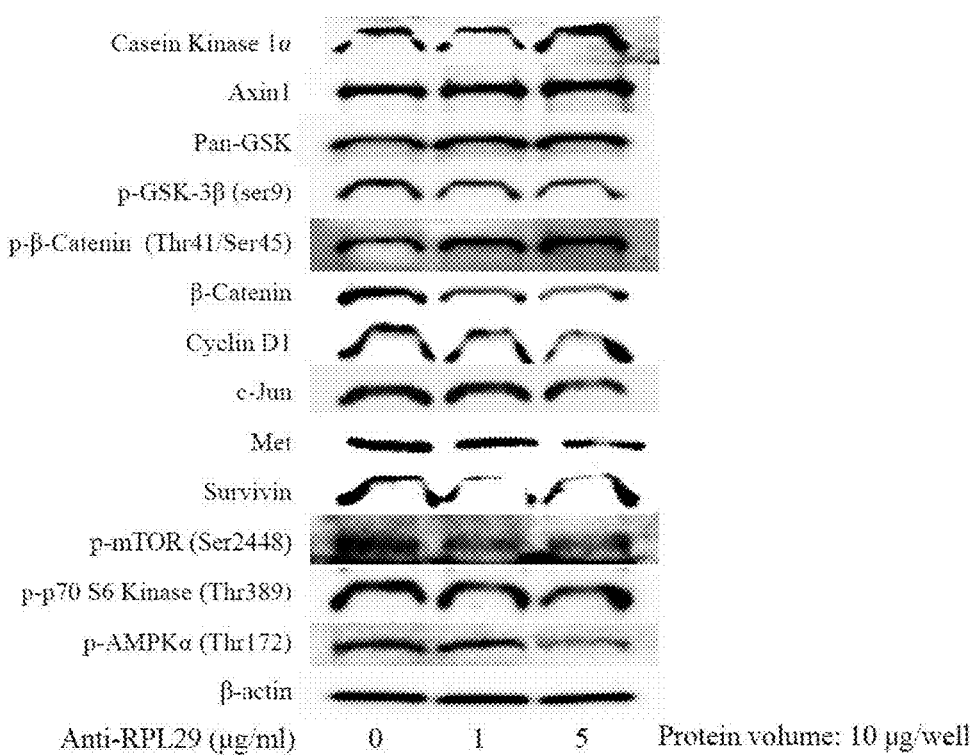
FIG. 12 Photographs confirming various intracellular signal changes in liver cancer cell strain Huh7 by the anti-RPL29 antibody (Example 4).

In a normal state, a β-Catenin accumulating in cells is transferred into the nucleus by Wnt stimulation and then promotes expression of genes of cyclin D1 and the like. In the absence of the Wnt stimulation, the β-Catenin binds to Axin together with APC and GSK-3β, is phosphorylated by the casein kinase 1α and GSK-3β and accordingly ubiquitinated in this Axin complex, and is eventually decomposed by a proteasome. In relation to cancer cells, it is considered that the β-catenin abnormally accumulates in the cytoplasm and the nuclear, and thus abnormal cell proliferation is induced via overexpression of cancer-related genes such as cyclin D1 and c-Jun, Met and Survivin (Cell Signal 2008; 20:1697, Oncogene 2012 17; 31:2580, Mol Cancer Res 2009; 7:1189). In the present embodiment, it was founded that administration of the anti-RPL29 antibody to the liver cancer cell strain Huh7 resulted in increased expression of GSK-3β, Axin 1, casein kinase 1α regulating the intracellular β-catenin toward decomposition, decreased β-catenin level in the cell, and decreased protein expression of the cyclin D1, c-Jun, Met and Survivin which are target genes (see FIG. 12).

When an intracellular serine/threonine kinase mTOR is activated by phosphorylation, mRNA translation and protein synthesis are promoted, and growth and proliferation of cells are induced (Cell 2012; 149:274). In the Example, it was found that activities of the intracellular mTOR and downstream effector p70 S6 kinase were lowered by administering the anti-RPL29 antibody to the liver cancer cell strain huh7 (see FIG. 12).

It has been reported that proliferation was suppressed in pancreas cancer cells (Int J Oncol 2012; 41:2227), large intestine cancer cells (J Surg Oncol 2012; 106:680) and prostate cancer cells (Mol Cancer Ther 2009; 8:733) by AMPK inhibition. Also in the present embodiment, it was found that activity of the intracellular AMPK was lowered in the liver cancer cell strain huh7 by administering the anti-RPL29 antibody (see FIG. 12).

(Example 5) Relationship Between the Serum Anti-RPL29 Antibody Titer and the Antiproliferative Effect of Serum IgG on Liver Cancer Cell Strain (1)

A liver cancer cell strain Huh7 or PLC/PRF/5 was adjusted to be $5.0 \times 10^4$ cell/ml, and was then inoculated on a 96 well plate for cell culture at 100 μl/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, in twenty-five cases among the patients with autoimmune hepatitis who were measured for the anti-RPL29 antibody in Reference Example 3, the purified IgG solution obtained by the same procedure as in Reference Example 1 was added to each well (5 μg/ml). As a control at this time, only the same amount of eluate (50 mM Glycine Buffer, pH 2.8) was added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. After addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 13:
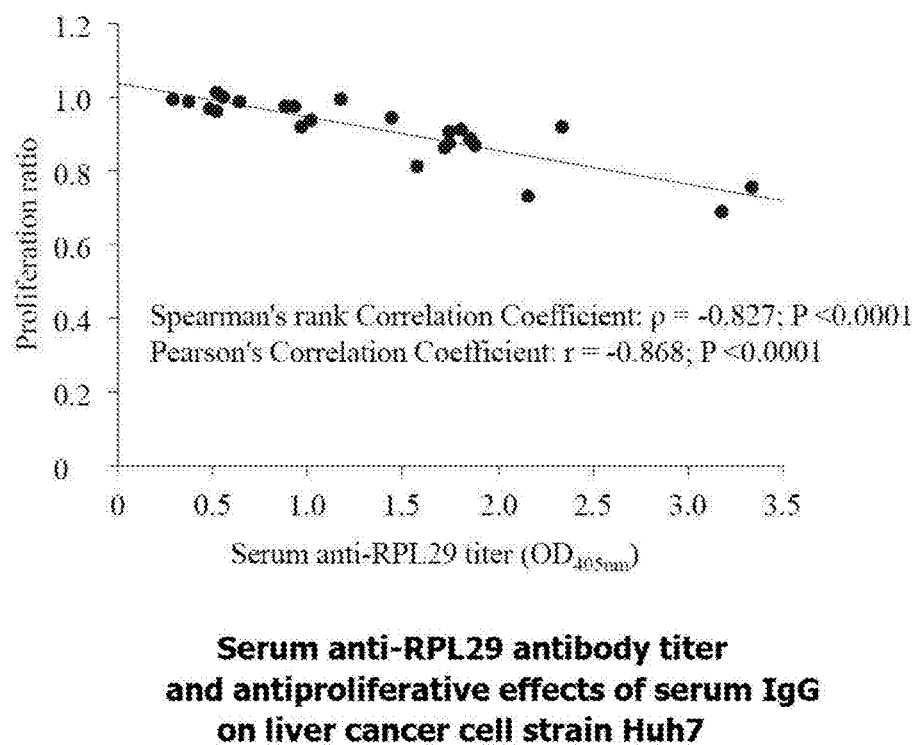
FIG. 13 A diagram showing a correlation between the serum anti-RPL29 antibody titer and antiproliferative effects of the serum IgG on liver cancer cell strain Huh7 (Example 5).
Figure 14:
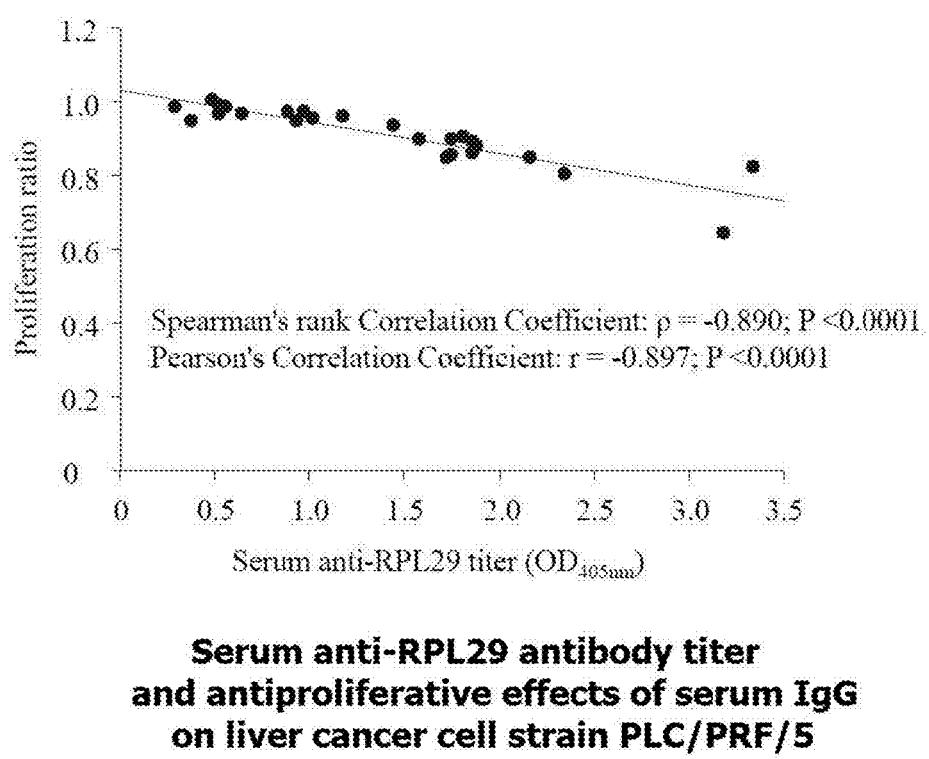
FIG. 14 A diagram showing a correlation between the serum anti-RPL29 antibody titer and antiproliferative effects of the serum IgG on liver cancer cell strain PLC/PRF/5 (Example 5).

In the patients with autoimmune hepatitis, there was found a strong correlation between the anti-RPL29 antibody titer of the serum IgG and the antiproliferative effect on the liver cancer cell strain. The results showed that the higher the anti-RPL29 antibody titer in the serum was, the higher the antiproliferative effect on the liver cancer cell was (see FIGS. 13 and 14). Consequently, it was considered that higher anti-tumor effects was able to be obtained by the increase in the amount of the serum anti-RPL29 antibody.

(Example 6) Relationship Between the Serum Anti-RPL29 Antibody Titer and the Antiproliferative Effect of the Serum IgG on Liver Cancer Cell Strain (2)

A liver cancer cell strain Huh7 or PLC/PRF/5 was adjusted to be $5.0 \times 10^4$ cell/ml, and was then inoculated on a 96 well plate for cell culture at 100 μl/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+ 1% penicillin-streptomycin solution (Sigma-Aldrich Co., MO). Twelve hours after the start of the culture, in four cases among the patients with autoimmune hepatitis who were measured for the anti-RPL29 antibody in Reference Example 3, 0 µg/ml or 5 µg/ml of IgG, and 0 µg/ml or 1 µg/ml of recombinant RPL29 (H00006159-P01: Avnova, Taipei, Taiwan) was added to the purified IgG solution obtained by the same procedure as in Reference Example 1. As a control at this time, only the same amount of eluate (50 mM Glycine Buffer, pH 2.8) was added. Sixty hours after the start of the culture, 10 µl of 3-(4,5-dimethylthiazol-2-yl)-2,5-diphenyl tetrazolium bromide (MTT: 5 mg/ml in phosphate buffered saline) solution was added to each well. After addition of the MTT, the culture solution was removed, and 100 µl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 15:
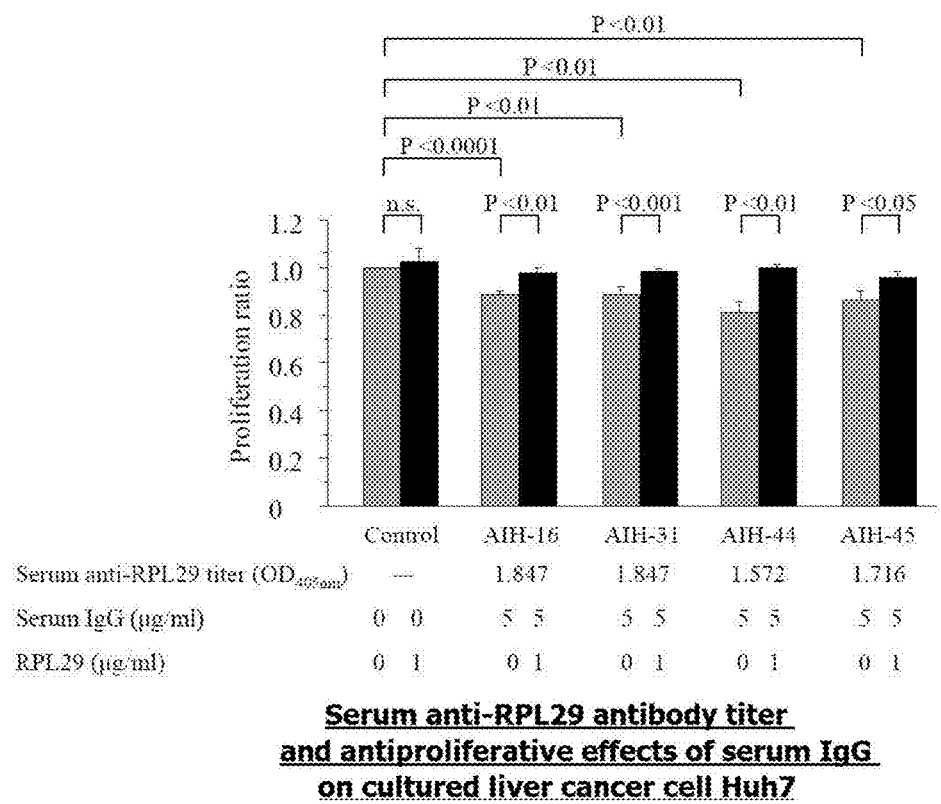
FIG. 15 A diagram showing the serum anti-RPL29 antibody titer and antiproliferative effects of the serum IgG on liver cancer cell strain Huh7 (Example 6).
Figure 16:
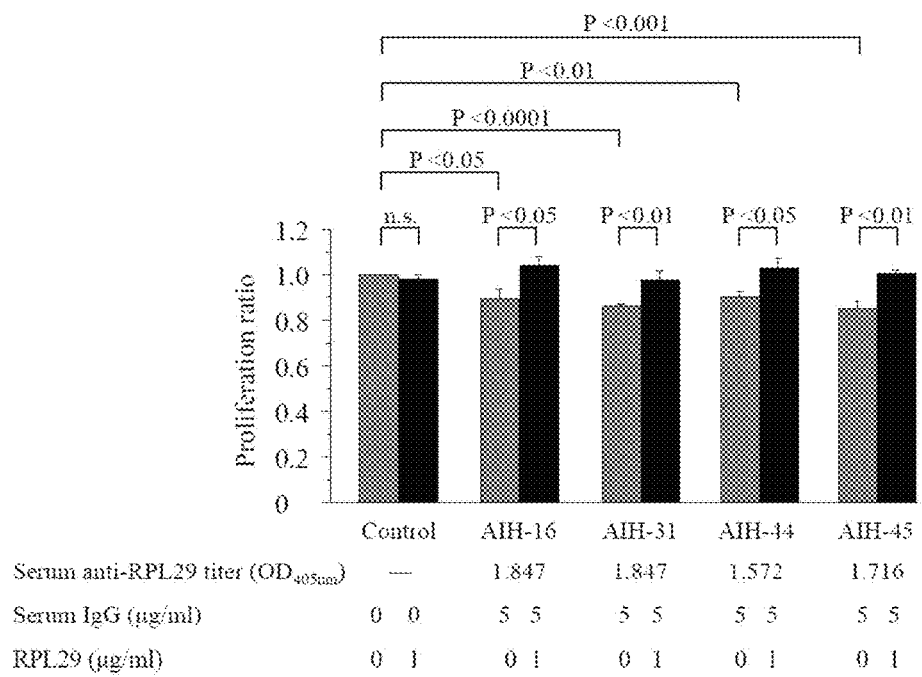
FIG. 16 A diagram showing the serum anti-RPL29 antibody titer and antiproliferative effects of the serum IgG on liver cancer cell strain PLC/PRF/5 (Example 6).

The cell antiproliferative effects of the IgG extracted from serum of the autoimmune hepatitis patients with high serum anti-RPL29 antibody titers on the liver cancer cell strain were offset by addition of the RPL29 (see FIGS. 15 and 16). The serum anti-RPL29 antibody titer was measured by the same procedure as in Reference Example 3. Therefore, it was confirmed that the substance exhibiting the antiproliferative effects on the liver cancer cells was the anti-RPL29 antibody. Consequently, a high level of the anti-RPL29 antibody was found in a living body by administering the anti-RPL29 antibodies or by administering a substance capable of activating or enhancing the endogenous anti-RPL29 antibody existing in the living body and a substance capable of inducing production of the anti-RPL29 antibodies in the living body, and thus effective anti-tumor effects can be expected.

(Example 7) Antiproliferative Effects of the Anti-RPL29 Antibody on Pancreas Cancer Cell Strain Panc-1

A pancreas cancer cell strain Panc-1 was adjusted to be $5.0 \times 10^4$ cell/ml, and was then inoculated on a 96 well plate for cell culture at 100 µl/well. Meanwhile, the culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, 0 µg/ml, 1 µg/ml or 5 µg/ml of anti-RPL29 antibody (H00006159-B02P:Avnova, Taipei, Taiwan) was added. Subsequently, twenty-four or forty-eight hours later (36 or 60 hours after the start of the culture), 10 µl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 µl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 17:
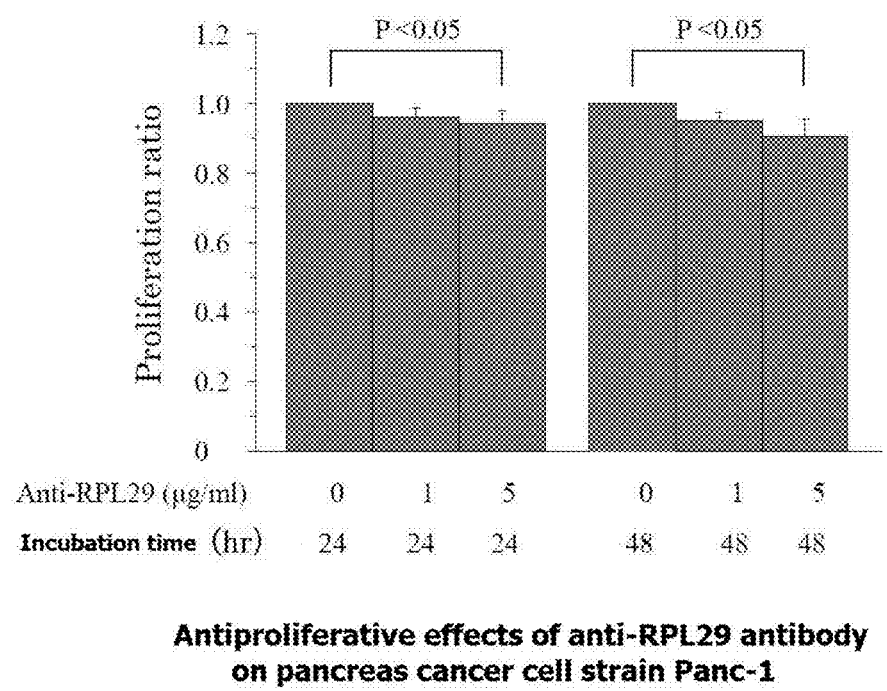
FIG. 17 A diagram showing antiproliferative effects of the anti-RPL29 antibody on pancreas cancer cell strain Panc-1 (Example 7).

The anti-RPL29 antibody inhibited cell proliferation of the pancreas cancer cell strain Panc-1 concentration-dependently and time-dependently (see FIG. 17).

(Example 8) Antiproliferative Effects of the Anti-RPL29 Antibody on Pancreas Cancer Cell Strain AsPC-1

A pancreas cancer cell strain AsPC-1 was adjusted to be $5.0 \times 10^4$ cell/ml, and was then inoculated on a 96 well plate for cell culture at 100 µl/well. Meanwhile, the culture solution was cultured at 37° C. under 5% $CO_2$ through the use of DMEM (Invitrogen Co., Carlsbad, Calif.)+10% heat-inactivated FES (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, 0 µg/ml, 1 µg/ml or 5 µg/ml of anti-RPL29 antibody (H00006159-B02P: Avnova, Taipei, Taiwan) was added. Sixty hours after the start of the culture, 10 µl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 µl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 18:
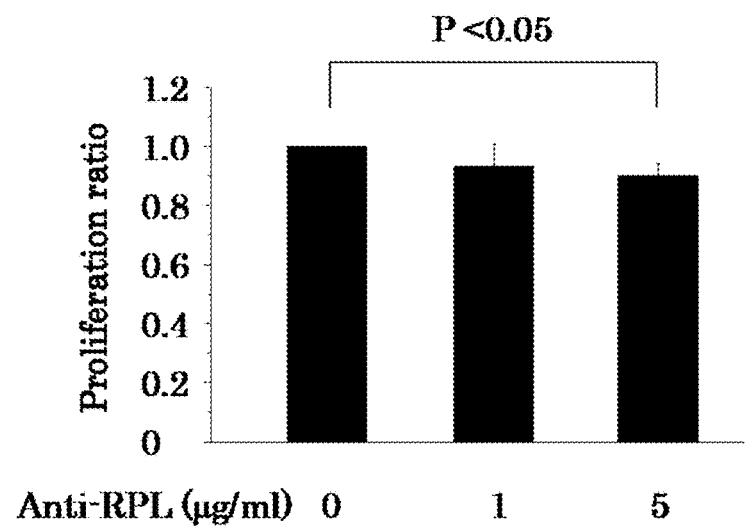
FIG. 18 A diagram showing antiproliferative effects of the anti-RPL29 antibody on pancreas cancer cell strain AsPC-1 (Example 8).

The anti-RPL29 antibody inhibited the cell proliferation of the pancreas cancer cell strain AsPC-1 concentration-dependently (see FIG. 18).

(Example 9) Intracellular Signal Change of Pancreas Cancer Cell Strain AsPC-1 by the Anti-RPL29 Antibody A pancreas cancer cell strain AsPC-1 was inoculated on a 10 cm plate for cell culture. Meanwhile, the culture solution was cultured at 37° C. under 5% $CO_2$ through the use of DMEM (Invitrogen Co., Carlsbad, Calif.)+10% heat-inactivated FES (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). In a condition of 60% confluent, 1 µg/ml of anti-RPL29 antibody (H00006159-B02P: Avnova, Taipei, Taiwan) was added. Forty eight hours after administration of the anti-RPL29 antibody, intracellular signals were analyzed through the use of Proteome Profiler™ Phospho-Kinase Array Kit (R&D Systems, Inc., MN, USA). Meanwhile, the anti-RPL29 antibody was not administered to a control.

Figure 19:
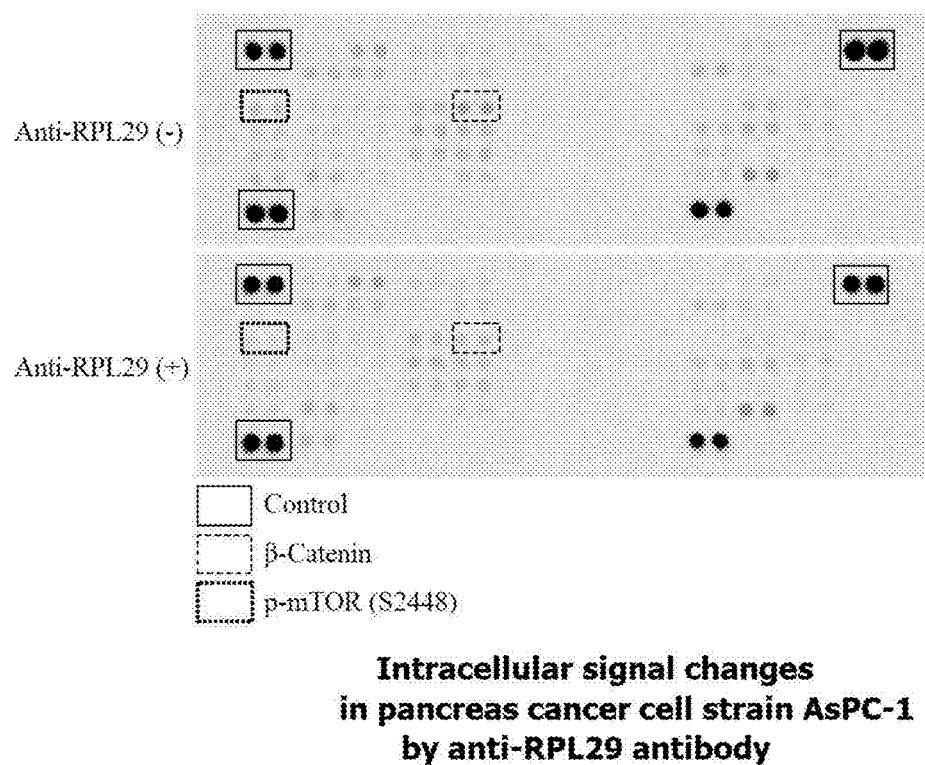
FIG. 19 Photographs showing various intracellular signal changes in pancreas cancer cell strain AsPC-1 by the anti-RPL29 antibody (Example 9).

In the pancreas cancer cell strain AsPC-1 dosed with the anti-RPL29 antibody, the decrease in intracellular β-catenin and p-mTOR (S2448) was found. The decreases indicate that the anti-RPL29 antibody inhibits an intracellular signaling system involved in the cell cycle and the cell proliferation (see FIG. 19).

(Example 10) The Serum Anti-RPL29 Antibody and Recurrence, in Patients Having Pancreas Cancer Resection In the present embodiment, in relation to cases of resectable pancreas cancer diagnosed as pancreas cancer by cytodiagnosis or tissue diagnosis and cases of having no distant metastatic focus, 31 patients who underwent curative resection of pancreas cancer primary focus were targeted. There was measured the serumanti-RPL29 antibody titer before curative resection by the same procedure as in Reference Example 3 and there was analyzed its relationship with a time period from the curative resection to recurrence of pancreas cancer by Kaplan-meier method, and thus the serum anti-RPL29 antibody titer and possibility of prognostic prediction were examined. The serum anti-RPL29 antibody titers were measured by the same procedure as in Reference Example 3.

Figure 20:
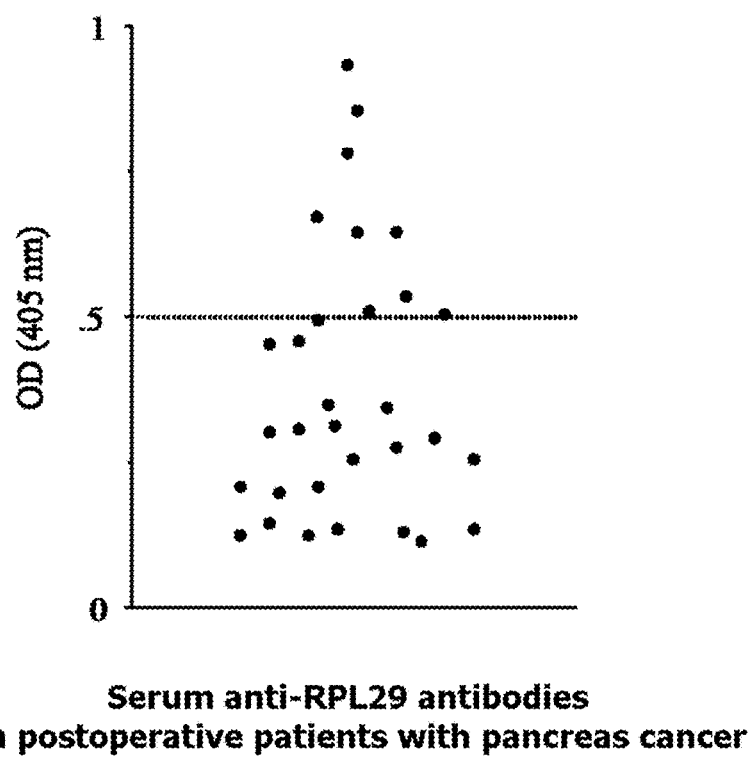
FIG. 20 A diagram showing the serum anti-RPL29 antibody titers in postoperative patients with pancreas cancer (Example 10).

The anti-RPL29 antibody titers in the patients having pancreas cancer resection were shown in FIG. 20. The serumanti-RPL29 antibody titers were classified into cases of 0.5 $OD_{405\ nm}$ or more and cases of less than 0.5 $OD_{405\ nm}$, and these patients' characteristics were shown in Table 3.

TABLE 3

Patient characteristics in cases of resected pancreas

| Anti-RPL29 titer | <0.5 $OD_{405\ nm}$ | ≥0.5 $OD_{405\ nm}$ | P |
|---|---|---|---|
| Patient, n | 22 | 9 | |
| Age, yr | 63 (34-85) | 70 (55-77) | 0.50 |
| Male, n (%) | 15 (68) | 3 (33) | 0.07 |
| Location of tumor, n (%) | | | 0.74 |
| Head | 16 (73) | 6 (67) | |
| Body or tail | 6 (27) | 3 (33) | |
| Stage (UICC), n (%) | | | 0.56 |
| IA | 2 (9) | 1 (11) | |
| IB | 2 (9) | 0 (0) | |
| IIA | 11 (50) | 4 (45) | |
| IIB | 6 (27) | 2 (22) | |
| III | 1 (5) | 2 (22) | |

Figure 21:
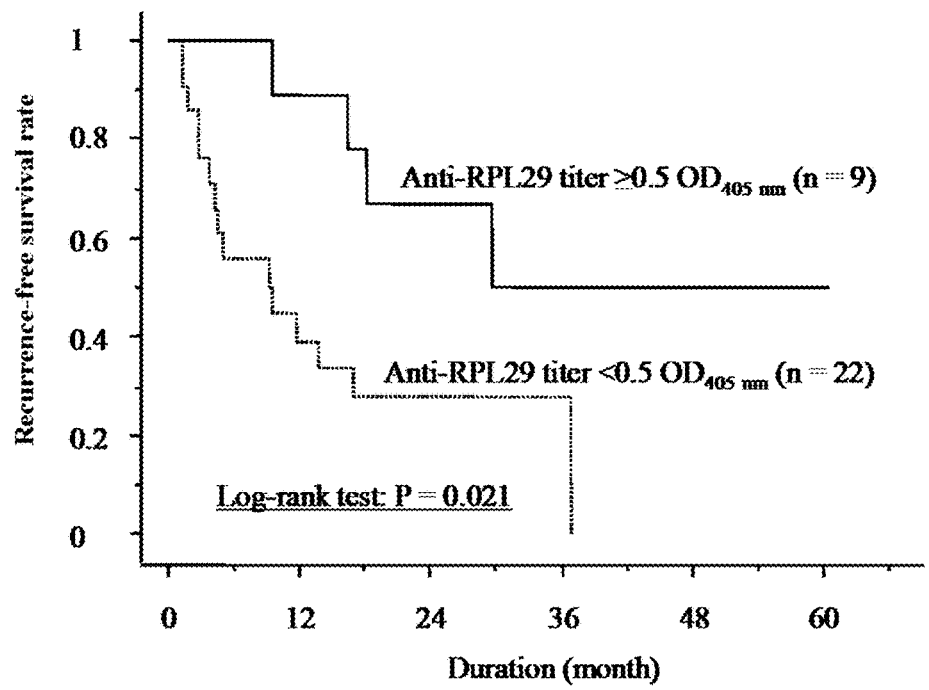
FIG. 21 A diagram showing a relationship between the serum anti-RPL29 antibody titer and postoperative recurrence in postoperative patients with pancreas cancer (Example 10).

There were no significant differences in the patients characteristics between the cases of the serum anti-RPL29 antibody titer of 0.5 $OD_{405\ nm}$ or more and those of less than 0.5 $OD_{405\ nm}$. However, the time period to postoperative recurrence in the cases of the serum anti-RPL29 antibody titer of 0.5 $OD_{405\ nm}$ or more was obviously longer than in the cases of the serum anti-RPL29 antibody titer of less than 0.5 $OD_{405\ nm}$ (see FIG. 21).

(Example 11) Antiproliferative Effects of the Serum IgG on Pancreas and Large Intestine Cancers A pancreas cancer cell strains AsPC-1 and Panc-1, and large intestine cancer cell strain HCT15 were adjusted to be 5.0×10⁴ cell/ml respectively, and were then inoculated on a 96 well plate for cell culture at 100 μl/well. Meanwhile, the culture solution for culturing the pancreas cancer cell strains was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). The culture solution for culturing the large intestine cancer cell strain was cultured in the same condition through the use of RPMI-1640 (Sigma-Aldrich Co., MO)+10% heat-inactivated FBS (Vitromex, Vilshofen, Germany)+1% penicillin-streptomycin solution (Sigma-Aldrich Co., MO). IgG was extracted from serum of two patients with autoimmune hepatitis (AIH-31 and AIH-45) exhibiting high serumanti-RPL29 antibody titers, in the same procedure as in Reference Example 1. Twelve hours after the start of the culture, 0 μg/ml or 5 μg/ml of the extracted IgG was added. Furthermore, 0 μg/ml or 1 μg/ml of recombinant RPL29 (H00006159-P01: Avnova, Taipei, Taiwan) was added. As a control, only the same amount of eluate (50 mM Glycine Buffer, pH 2.8) was added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 22:
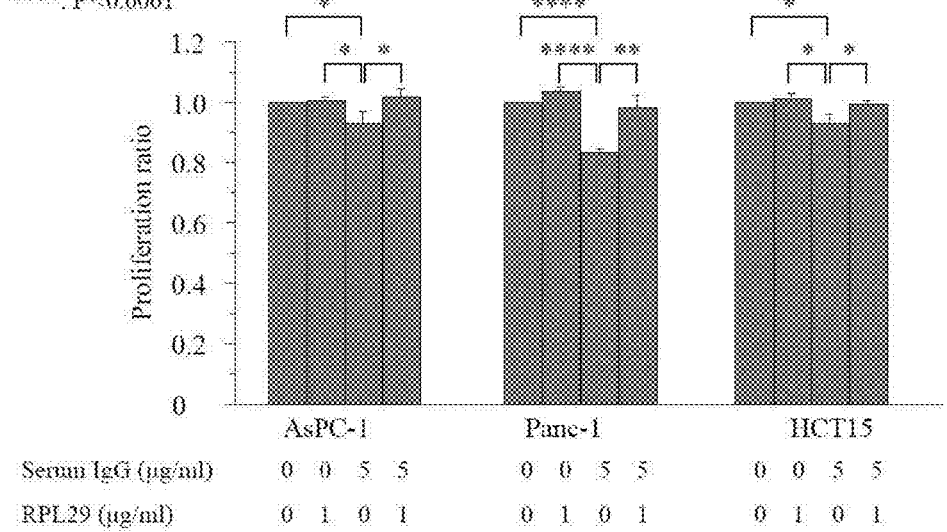
FIG. 22 A diagram showing antiproliferative effects of the serum IgG of AIH-31 on pancreas cancer cell strain and large intestine cancer cell strain (Example 11).
Figure 23:
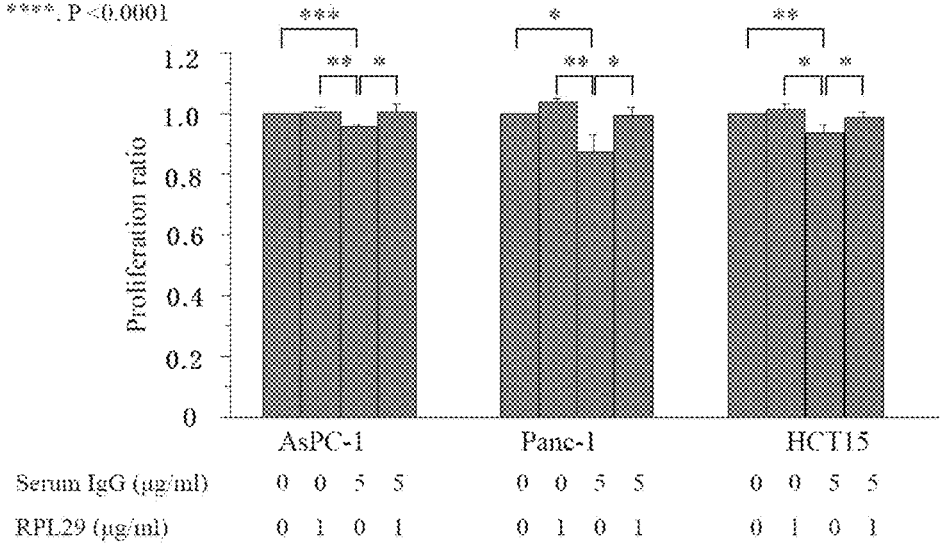
FIG. 23 A diagram showing antiproliferative effects of the serum. IgG of AIH-45 on pancreas cancer cell strain and large intestine cancer cell strain (Example 11).

In the IgG extracted from serum of the autoimmune hepatitis patients with high serum anti-RPL29 antibody titers, antiproliferative effects targeting RPL29 in pancreas and large intestine cancers (see FIG. 22, 23) were found. In addition, it was also observed that the antiproliferative effects were offset by addition of a recombinant RPL29. Therefore, it was confirmed that the substance exhibiting the antiproliferative effects on the pancreas and large intestine cancers was the anti-RPL29 antibody. Consequently, a high level of the anti-RPL29 antibody was found in a living body by administering the anti-RPL29 antibodies or by administering a substance capable of activating or enhancing the endogenous anti-RPL29 antibody existing in the living body and a substance capable of inducing production of the anti-RPL29 antibodies in the living body, and thus effective anti-tumor effects can be expected.

(Example 12) Antiproliferative Effects of the Serum IgG on Various Human Malignant Tumor Cells A breast cancer cell strain MCF-7 or a cultured small cell lung cancer strain H1048, a non-small cell lung cancer cell strain PC-9 and a prostate cancer cell strain PC-3 were adjusted to be 5.0×10⁴ cell/ml respectively, and were then inoculated on a 96 well plate for cell culture at 100 μl/well. Meanwhile, the culture solution was cultured at 37° C. under 5% $CO_2$ through the use of RPMI-1640 (Sigma-Aldrich Co., MO)+10% heat-inactivated FBS (Vitromex, Vilshofen, Germany)+1% penicillin-streptomycin solution (Sigma-Aldrich Co., MO). Twelve hours after the start of the culture, 0 μg/ml or 5 μg/ml of the IgG extracted from serum of two patients with autoimmune hepatitis (AIH-31, AIH-45) having high level of serum anti-RPL29 antibody, in the same procedure as in Reference Example 1, was added. As a control, only the same amount of eluate (50 mM Glycine Buffer, pH 2.8) was added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 24:
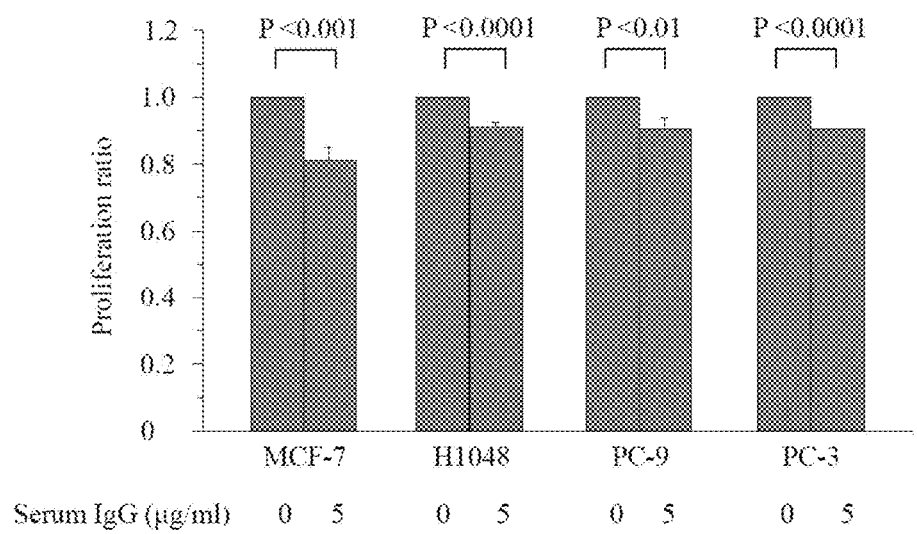
FIG. 24 A diagram showing antiproliferative effects of the serum IgG of AIH-31 on various malignant tumor cell strains (Example 12).
Figure 25:
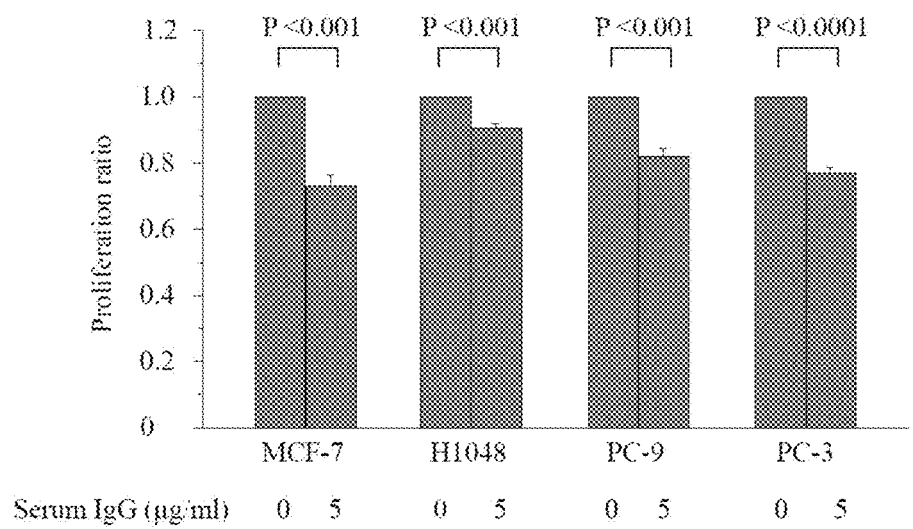
FIG. 25 A diagram showing antiproliferative effects of the serum IgG of AIH-45 on various malignant tumor cell strains (Example 12).

In the IgG extracted from serum of the autoimmune hepatitis patients with high serum anti-RPL29 antibody titers, antiproliferative effects against breast cancer, small cell lung cancer, non-small cell lung cancer and prostate cancer were found (see FIGS. 24 and 25).

(Example 13) Antiproliferative Effects of the Anti-RPL29 Antibody on Various Human Malignant Tumor Cells Antiproliferative effects of the anti-RPL29 antibody on various human malignant tumor cells (large intestine cancer, small cell lung cancer, non-small cell lung cancer, breast cancer, prostate cancer, and pancreas cancer) were examined.

Abreast cancer cell strain MCF-7 or a large intestine cancer cell strain HCT15, a non-small cell lung cancer cell strain PC-9, a small cell lung cancer cell strain H1048 and a prostate cell strain PC-3 were adjusted to be 5.0×10⁴ cell/ml, and were then inoculated on a 96 well plate for cell culture at 100 μl/well. Meanwhile, the culture solution was cultured at 37° C. under 5% $CO_2$ through the use of RPM-1640 (Sigma-Aldrich Co., MO)+10% heat-inactivated FBS (Vitromex, Vilshofen, Germany)+1% penicillin-streptomycin solution (Sigma-Aldrich Co., MO). Twelve hours after the start of the culture, 0 μg/ml, 1 μg/ml or 5 μg/ml of anti-RPL29 antibody (H00006159-B02P: Avnova, Taipei, Taiwan) was added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 26:
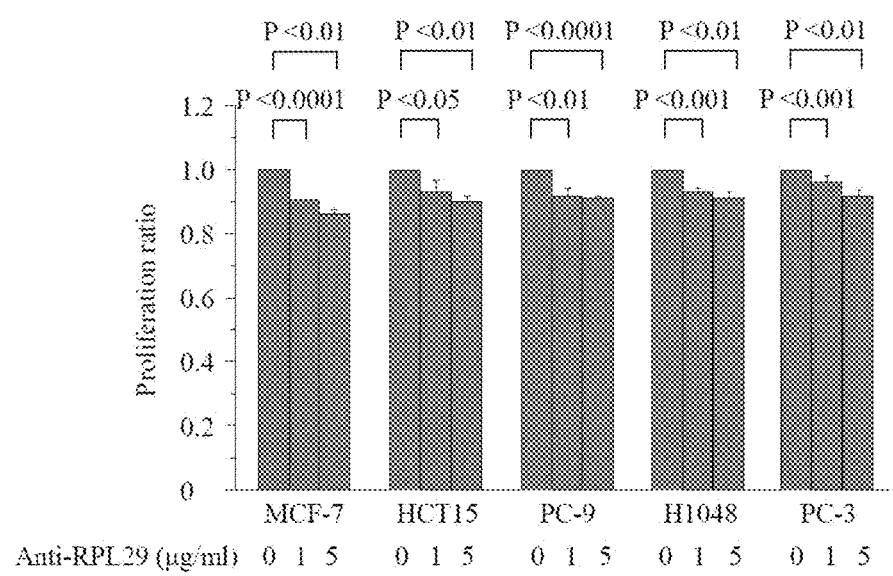
FIG. 26 A diagram showing antiproliferative effects of the anti-RPL29 antibody on various human malignant tumor cell strains (Example 13).

The anti-RPL29 antibody inhibited the cell proliferations of the breast cancer cells, large intestine cancer cells, non-small cell lung cancer, small cell lung cancer, and prostate cancer (see FIG. 26).

(Example 14) Antiproliferative Effects of the Anti-RPS4X Antibody on Liver Cancer Cell Strain Huh7

A liver cancer cell strain Huh7 was adjusted to be $5.0 \times 10^4$ cell/ml, and was then inoculated on a 96 well plate for cell culture at 100 μl/well. The culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, 0 μg/ml, 1 μg/ml or 5 μg/ml of anti-RPS4X antibody (PAB17574: Avnova, Taipei, Taiwan) was added. Twenty-four or forty-eight hours later (36 or 60 hours after the start of the culture), 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 27:
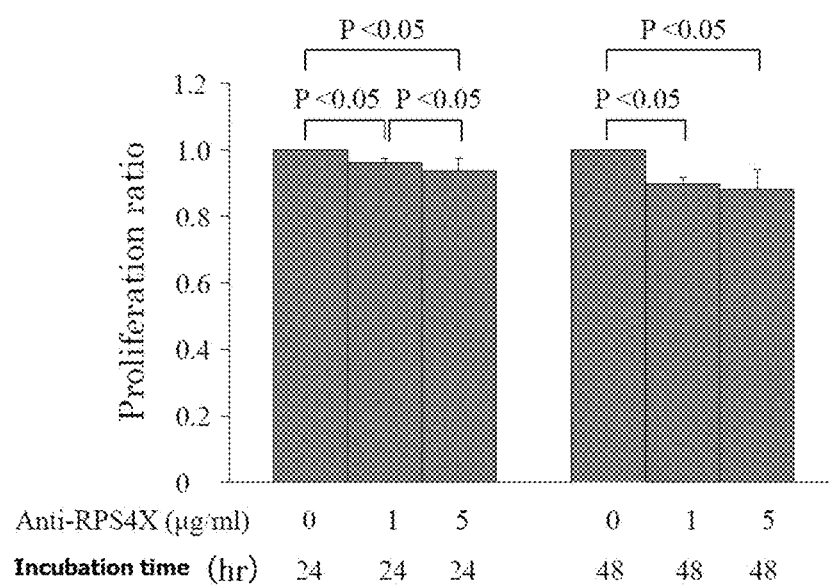
FIG. 27 A diagram showing antiproliferative effects of the anti-RPS4X antibody on liver cancer cell strain Huh? (Example 14).

The anti-RPS4X antibody inhibited cell proliferation of the liver cancer cell strain Huh7 concentration-dependently and time-dependently (see FIG. 27).

(Example 15) Antiproliferative Effects of the Anti-RPS4X Antibody on Malignant Tumor Cells (Liver Cancer and Pancreas Cancer)

A liver cancer cell strain PLC/PRF/5 or a pancreas cancer cell strains Panc-1 and AsPC-1 was adjusted to be $5.0 \times 10^4$ cell/ml, and was then inoculated on a 96 well plate for cell culture at 100 μl/well. The culture solution was cultured at 37° C. under 5% $CO_2$ through the use of DMEM (Invitrogen Co., Carlsbad, Calif.)+10% heat-inactivated FBS (Vitromex, Vilshofen, Germany)+1% non-essential amino acid (Sigma-Aldrich Co., MO)+1% sodium pyruvate (Sigma-Aldrich Co., MO)+1% penicillin-streptomycin solution (Sigma-Aldrich Co., MO). Twelve hours after the start of the culture, 0 μg/ml, 1 μg/ml or 5 μg/ml of anti-RPS4X antibody (PAB17574: Avnova, Taipei, Taiwan) was added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 28:
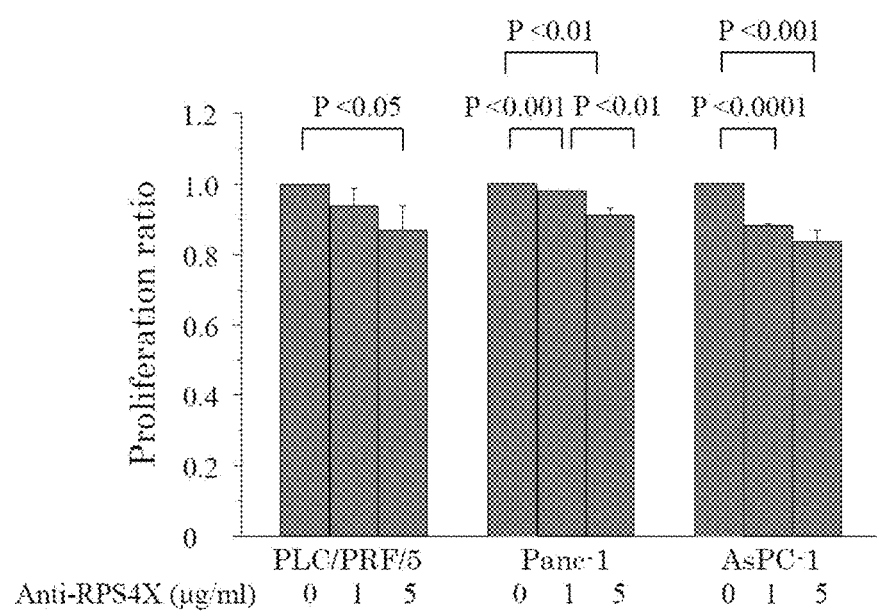
FIG. 28 A diagram showing antiproliferative effects of the anti-RPS4X antibody on liver cancer cell strain and pancreas cancer cell strain (Example 15).

The anti-RPS4X antibody inhibited the cell proliferation of the liver cancer cell and pancreas cancer cell concentration-dependently (see FIG. 28).

(Example 16) Examination of Antiproliferative Effects of the Anti-RPS4X Antibody on Various Malignant Tumor Cells Antiproliferative effects of the anti-RPS4X antibody on various malignant tumor cells (large intestine cancer, small cell lung cancer, non-small cell lung cancer, breast cancer, and prostate cancer) were examined.

A breast cancer cell strain MCF-7 or a large intestine cancer cell strain HCT15, a non-small cell lung cancer cell strain PC-9, a small cell lung cancer cell strain H1048 and a prostate cancer cell strain PC-3 were adjusted to be $5.0 \times 10^4$ cell/ml respectively, and were then inoculated on a 96 well plate for cell culture at 100 μl/well. Meanwhile, the culture solution was cultured at 37° C. under 5% $CO_2$ through the use of RPMI-1640 (Sigma-Aldrich Co., MO)+10% heat-inactivated FBS (Vitromex, Vilshofen, Germany)+1% penicillin-streptomycin solution (Sigma-Aldrich Co., MO). Twelve hours after the start of the culture, 0 μg/ml, 1 μg/ml or 5 μg/ml of anti-RPS4X antibody (PAB17574: Avnova, Taipei, Taiwan) was added. Sixty hours after the start of the culture, 10 μl of 3-(4,5-dimethylthiazol-2-yl)-2,5-diphenyl tetrazolium bromide (MTT: 5 mg/ml in phosphate buffered saline) solution was added to each well. Four hours after addition of the MTT, the culture solution was removed, and 100 μl of DMSO was added to each well. The absorbance at 570 nm was measured by an ELISA reader (Model 680 Microplate Reader: Bio-Rad Laboratories Ltd., Tokyo, Japan). The absorbance in each condition was represented by a ratio to a control.

Figure 29:
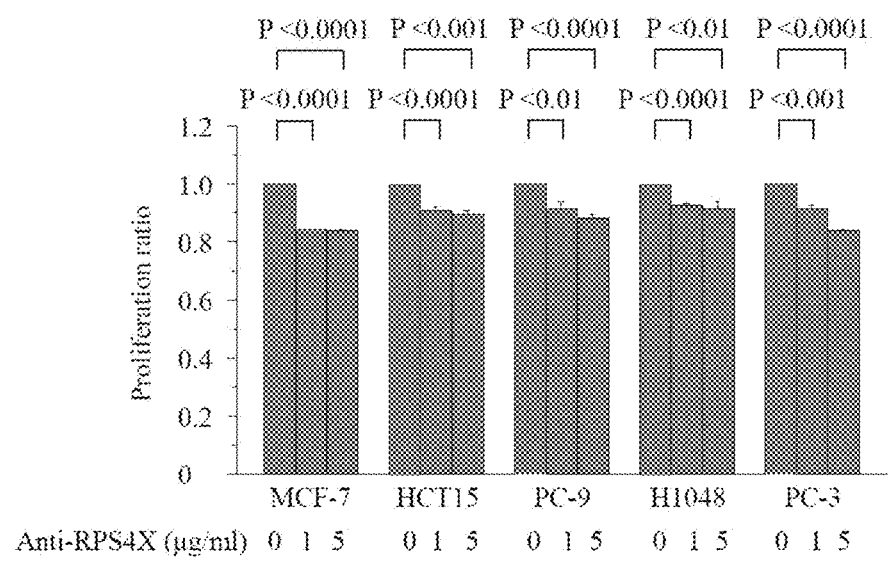
FIG. 29 A diagram showing antiproliferative effects of the anti-RPS4X antibody on various human malignant tumor cell strains (Example 16).

The anti-RPS4X antibody inhibited the cell proliferation of the breast cancer cells, large intestine cancer cells, non-small cell lung cancer, small cell lung cancer, and prostate cancer (see FIG. 29).

INDUSTRIAL APPLICABILITY

As described above in detail, the anti-malignant tumor agent of the present invention which characteristically contains, as an active ingredient, a substance targeting ribosomal proteins showing increased expression in a malignant tumor cell can inhibit growth of the malignant tumor cells. The substance of the present inventions targeting the ribosomal protein showing increased expression in the malignant tumor cell may be a substance involved in one of biological defense mechanisms which are considered to be intrinsically provided in a living body and prevent onset of disease even if malignant tumor cells develop. An anti-malignant tumor agent which contains such a substance as an active ingredient is a drug having high safety and is useful.

Additionally, in the examination method of the present invention, prognosis of a cancer patient can also be predicted by measuring an amount of the substance targeting ribosomal proteins showing increased expression in a malignant tumor cell, for example, an antibody titer in a case of an antibody, and the substance is very useful in that an optimal therapy can be given to the cancer patient depending on the results.

The invention claimed is:

1. A method of monitoring prognosis of a cancer treatment in a subject, the method comprising:
   measuring a ribosome antibody titer determined by measuring an anti-RPL29 antibody titer, an anti-RPS4X antibody titer, or both in a biospecimen obtained from the subject;
   performing at least one anti-cancer treatment on the subject comprising (i) performing a resection operation of cancer on the subject or (ii) administering to the subject an anti-malignant tumor agent containing, as an active ingredient, (a) an anti-RPL29 antibody, (b) an anti-RPS4X antibody, or (c) gemcitabine, or any combination of (a), (b), and (c); and
   determining a prognosis of the subject based on the ribosome antibody titer measured.

2. The method of claim 1, wherein the ribosome antibody titer is determined by measuring the anti-RPL29 antibody titer.

3. The method of claim 1, wherein the anti-RPS4X antibody titer is measured.

4. The method of claim 1, wherein the biospecimen comprises at least one of blood, blood plasma, blood serum, spinal fluid, lymph, urine, tears, or milk.

5. The method of claim 1, wherein the determining comprises determining a cut-off value for the antibody titer measured, an antibody titer above the cut-off value determining a positive prognosis, and an antibody titer below the cut-off value determining a negative prognosis.

6. The method of claim 5, wherein the positive prognosis comprises a low recurrence rate of a malignant cancer, a high post-treatment survival rate, or both, and the negative prognosis comprises a high recurrence rate of the malignant cancer, a low post-treatment survival rate, or both.

7. The method of claim 1, further comprising diagnosing the subject with at least one cancer.

8. The method of claim 7, wherein the at least one cancer comprises a malignant tumor.

9. The method of claim 8, wherein the malignant tumor expresses at least one of a RPL29 protein and a RPS4X protein at a level higher than a non-malignant cell.

10. The method of claim 7, wherein the at least one cancer is one or a plurality of cancers selected from liver cancer, pancreas cancer, breast cancer, large intestine cancer, non-small cell lung cancer, small cell lung cancer, prostate cancer, gastric cancer, thyroid cancer, ovarian cancer, salivary gland adenoid cystic carcinoma, acute myeloid leukemia, acute lymphocytic leukemia, chronic lymphocytic leukemia, chronic myeloid leukemia, malignant lymphoma, myxoid liposarcoma, glioblastoma, alveolar rhabdomyosarcoma, Wilms tumor, oligodendroglioma, adrenocortical carcinoma, multiple myeloma, medulloblastoma, endometrial cancer, esophageal cancer and Ewing's sarcoma.

11. The method of claim 7, wherein the at least one cancer is one or a plurality of cancers selected from liver cancer, pancreas cancer, breast cancer, large intestine cancer, non-small cell lung cancer, small cell lung cancer and prostate cancer.

* * * * *